(12) United States Patent  
Akiyama

(10) Patent No.: US 7,517,828 B2  
(45) Date of Patent: Apr. 14, 2009

(54) CHIRAL BROENSTED ACID CATALYST FOR ASYMMETRIC SYNTHESIS AND METHOD OF ASYMMETRIC SYNTHESIS WITH THE CATALYST

(75) Inventor: Takahiko Akiyama, Tokyo (JP)

(73) Assignee: Toagosei Co., Ltd., Tokyo (JP)

( * ) Notice: Subject to any disclaimer, the term of this patent is extended or adjusted under 35 U.S.C. 154(b) by 44 days.

(21) Appl. No.: 10/554,369

(22) PCT Filed: Apr. 20, 2004

(86) PCT No.: PCT/JP2004/005602

§ 371 (c)(1),  
(2), (4) Date: Oct. 25, 2005

(87) PCT Pub. No.: WO2004/096753

PCT Pub. Date: Nov. 11, 2004

(65) Prior Publication Data

US 2006/0276329 A1 Dec. 7, 2006

(30) Foreign Application Priority Data

Apr. 25, 2003 (JP) ............................. 2003-121706

(51) Int. Cl.  
*B01J 31/00* (2006.01)

(52) U.S. Cl. .................. 502/150; 502/162; 556/13; 556/404

(58) Field of Classification Search ............. 502/150, 502/162; 556/13, 404  
See application file for complete search history.

(56) References Cited

U.S. PATENT DOCUMENTS 6,274,745 B1 * 8/2001 Inanaga et al. ............. 549/416  
6,391,926 B2 * 5/2002 Inanaga .................... 514/732

FOREIGN PATENT DOCUMENTS

| EP | 305089 | * | 3/1989 |
| EP | 1134209 | * | 9/2001 |
| JP | 2000-336097 A | | 12/2000 |
| JP | 2001-328995 A | | 11/2001 |

OTHER PUBLICATIONS

Furuno et al., Synthesis of novel rare earth metal complexes bearing chiral binaphthyldiyl phosphate derivatives as an asymmetric catalyst, Kidorui (1999), 34, 306-307.*  
Hodgson et al., Efficient RhII binaphthol phosphate catalysts for enantioselective intramolecular tandem carbonyl ylide formation-cycloaddition of -diazo- -keto esters, Chem. Commun., 1999, 2185-2186.*  
Jin et al., Chiral rare earth metal complex-catalyzed conjugate addition of O-alkyl hydroxylamines. An efficient synthetic entry into optically active 2-acyl aziridines, Tetrahedron (2002), 58(41), 8321-8329.*

Hodgson et al., Development of dirhodium(II)-catalyzed generation and enantioselective 1,3-dipolar cycloaddition of carbonyl ylides, Chemistry-A European Journal (2001), 7(20), 4465-4476.*  
Takahiko Akiyama, et al., "Enantioselective Mannich-Type Reaction Catalyzed by a Chiral Brønsted Acid", Angewandte Chemie International Edition, 2004, pp. 1566-1568, vol. 43, No. 12.  
Daisuke Uraguchi, et al., "Chiral Brønsted Acid-Catalyzed Direct Mannich Reactions via Electrophilic Activation", Journal of the American Chemical Society, 2004, pp. 5356-5357, vol. 126, No. 17.  
Benjamin List, et al., "Proline-Catalyzed Direct Asymmetic Aldol Reactions," Journal of the American Chemical Society, 2000, pp. 2395-2396, vol. 122, No. 10.  
Wolfgang Notz, et al., "Catalytic Asymmetric Synthesis of anti-1,2-Diols", Journal of the American Chemical Society, 2000, pp. 7386-7387, vol. 122, No. 30.  
Kandasamy Sakthivel, et al., "Amino Acid Catalyzed Direct Asymmetric Aldol Reactions: A Bioorganic Approach to Catalytic Asymmetric Carbon-Carbo Bond-Forming Reactions", Journal of the American Chemical Society, 2001, pp. 5260-5267, vol. 123, No. 22.  
Alan B. Northrup, et al., "The First Direct and Enantioselective Cross-Aldol Reaction of Aldehydes", Journal of the American Chemical Society, 2002, pp. 6798-6799, vol. 124, No. 24.

(Continued)

*Primary Examiner*—Daniel M Sullivan  
*Assistant Examiner*—Chukwuma O Nwaonicha  
(74) *Attorney, Agent, or Firm*—Sughrue Mion, PLLC

(57) ABSTRACT

A compound usable as an asymmetric synthesis catalyst which can be easily synthesized without using any metal such as a lanthanoid group element; a method of asymmetric synthesis with the compound; and a chiral compound obtained by the asymmetric synthesis method. A Broensted acid is used as a catalyst in asymmetric synthesis, the chiral Broensted acid being represented by formula (1) below or formula (3) below. The asymmetric synthesis method employs the catalyst. Asymmetric synthesis with the catalyst gives a chiral compound.

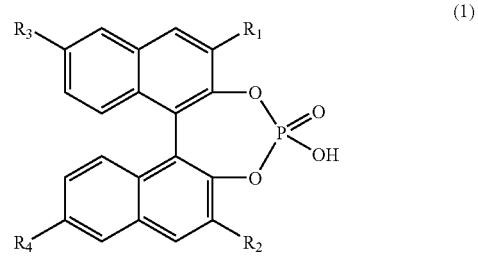

(1)

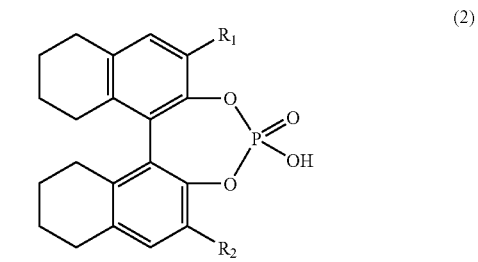

(2)

5 Claims, No Drawings

OTHER PUBLICATIONS

Anna G. Wenzel, et al., "Asymmetric Catalytic Mannich Reactions Catalyzed by Urea Derivatives" Enantioselective Synthesis of β-Aryl-β-Amino Acids, J. Am. Chem. Soc., 2002, pp. 12964-12965, vol. 124.

Daisuke Uraguchi, et al., "Organocatalytic Asymmetric Aza-Friedel—Crafts Alkylation of Furan", Journal of American Chemical Society, 2004, pp. 11804-11805, vol. 126.

"The Ninth International Kyoto Conference on New Aspects of Organic Chemistry", Nov. 10-14, 2003, pp. 116, PA-004.

"The Collection of lecture summaries of the 46$^{th}$ symposium of the Society of Synthetic Organic Chemistry, Kanto Branch", Nov. 22-23, 2003, pp. 67-68.

XP-002049944 (1995) Junji Inanaga et al., "Achiral and chiral lanthanide(III) salts of superacids as novel Lewis acid catalysts in organic synthesis", New J. Chem., vol. 19, No. 5/6 pp. 707-712.

Patent Abstracts of Japan, Junji Inanaga (2002), vol. 2002, No. 07, abstract of JP-A-2002-069066.

Supplementary European Search Report dated Oct. 10, 2006.

* cited by examiner

CHIRAL BROENSTED ACID CATALYST FOR ASYMMETRIC SYNTHESIS AND METHOD OF ASYMMETRIC SYNTHESIS WITH THE CATALYST

TECHNICAL FIELD

The present invention relates to a catalyst for use in asymmetric synthesis, and a method of asymmetric synthesis using the catalyst. Chiral compounds obtained by the method of the present invention are useful as compounds used in pharmaceuticals, agrochemicals, etc., or synthetic intermediates therefor.

BACKGROUND ART

A Diels-Alder cyclization reaction using a metal salt of a chiral binaphthol-phosphoric acid derivative is known (e.g. JP-A-2000-336097; JP-A denotes a Japanese unexamined patent application publication), but there is no known asymmetric synthesis method using a chiral binaphthol-phosphoric acid derivative that is not a metal salt, namely, a chiral Broensted acid. Furthermore, a chiral compound has been synthesized by carrying out an asymmetric Mannich reaction using a chiral urea derivative (ref., e.g. Anna G. Wenzel et al., "Asymmetric Catalytic Mannich Reactions Catalyzed by Urea Derivatives: Enantioselective Synthesis of β-Aryl-β-Amino Acids", Journal of The American Chemical Society, 124, 12964-5 (2002)).

DISCLOSURE OF INVENTION

Some conventional methods of asymmetric synthesis, such as an asymmetric Mannich reaction and an asymmetric aza Diels-Alder reaction, can give a product with high optical purity, but in these reactions it is essential to use a metal such as a lanthanoid group element. Under such circumstances, it is to provide a compound that can be used as an asymmetric synthesis catalyst that enables the synthesis to be carried out easily without using a metal such as a lanthanoid group element, a method of asymmetric synthesis using said compound, and a chiral compound obtained by said method of asymmetric synthesis.

In order to solve the above-mentioned problems, the present inventor has carried out an intensive investigation into the development of an asymmetric synthesis catalyst that can be used under practical reaction conditions and gives high optical purity. As a result, it has been found that by the use of a chiral Broensted acid as a catalyst a compound having high optical purity can be synthesized, and the present invention has thus been accomplished. This chiral Broensted acid is a chiral binaphthol-phosphoric acid derivative and is, for example, a chiral binaphthol-phosphoric acid derivative represented by formula (1) below or formula (3) below. The present invention is also a method of asymmetric synthesis using the chiral Broensted acid as a catalyst.

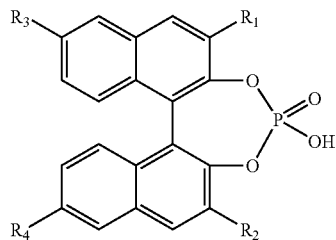

In formula (1) above, $R_1$, $R_2$, $R_3$, and $R_4$ may be independent of each other, and denote a hydrogen atom; a halogen atom; a nitro group; a monohalogenomethyl group; a dihalogenomethyl group; a trihalogenomethyl group; a nitrile group; a formyl group; —$COA_1$ ($A_1$ denotes an optionally branched alkyl group having 1 to 6 carbons); —$COOA_2$ ($A_2$ denotes an optionally branched alkyl group having 1 to 6 carbons); an optionally branched alkyl group having 1 to 20 carbons; an optionally branched alkenyl group having 3 to 20 carbons; an optionally branched alkoxy group having 1 to 20 carbons; an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), —$COOA_2$ ($A_2$ denotes an optionally branched alkyl group having 1 to 6 carbons), an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), —$COOA_2$ ($A_2$ denotes an optionally branched alkyl group having 1 to 6 carbons), and an optionally branched alkyl group having 1 to 20 carbons; a cycloalkyl group having 3 to 8 carbons; or formula (2) below.

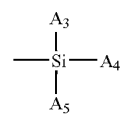

$A_3$, $A_4$, and $A_5$ of formula (2) may be independent of each other, and denote an optionally branched alkyl group having 1 to 6 carbons, a phenyl group, or a phenyl group mono- to tetra-substituted with an optionally branched alkyl group having 1 to 6 carbons.

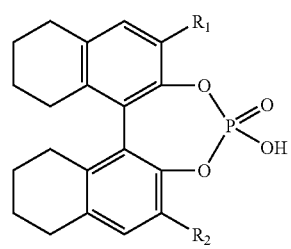

In formula (3), $R_1$ and $R_2$ may be independent of each other, and denote a hydrogen atom; a halogen atom; a nitro group; a monohalogenomethyl group; a dihalogenomethyl group; a trihalogenomethyl group; a nitrile group; a formyl group; —$COA_1$ ($A_1$ denotes an optionally branched alkyl group having 1 to 6 carbons); —$COOA_2$ ($A_2$ denotes an optionally branched alkyl group having 1 to 6 carbons); an optionally branched alkyl group having 1 to 20 carbons; an optionally branched alkenyl group having 3 to 20 carbons; an optionally branched alkoxy group having 1 to 20 carbons; an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —COA$_1$ (A$_1$ denotes an optionally branched alkyl group having 1 to 6 carbons), —COOA$_2$ (A$_2$ denotes an optionally branched alkyl group having 1 to 6 carbons), an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —COA$_1$ (A$_1$ denotes an optionally branched alkyl group having 1 to 6 carbons), —COOA$_2$ (A$_2$ denotes an optionally branched alkyl group having 1 to 6 carbons), and an optionally branched alkyl group having 1 to 20 carbons; a cycloalkyl group having 3 to 8 carbons; or formula (2).

The present invention is a method of asymmetric synthesis using as a catalyst a compound of formula (1) or formula (3).

The present invention is a chiral compound obtained by a method of asymmetric synthesis using as a catalyst a chiral Broensted acid, a chiral binaphthol-phosphoric acid derivative, or a compound of formula (1) or formula (3).

The present invention is a method for producing a chiral amino compound from an imine derivative and an enol derivative using as a catalyst a chiral Broensted acid, a chiral binaphthol-phosphoric acid derivative, or a compound of formula (1) or formula (3).

The present invention is a chiral amino compound obtained by the above-mentioned production method.

The present invention is an asymmetric Mannich reaction using as a catalyst a compound of formula (1) or formula (3).

The present invention is an asymmetric hydrophosphorylation reaction using as a catalyst a compound of formula (1) or formula (3).

The present invention is an asymmetric aza Diels-Alder reaction using as a catalyst a compound of formula (1) or formula (3).

The present invention is an asymmetric allylation reaction using as a catalyst a compound of formula (1) or formula (3).

The present invention is an asymmetric Strecker reaction using as a catalyst a compound of formula (1) or formula (3).

The present invention is an asymmetric aminoalkylation reaction using as a catalyst a compound of formula (1) or formula (3).

BEST MODE FOR CARRYING OUT THE INVENTION

The present invention is explained in detail below. In the explanation below, iso- is abbreviated to 'i-' and tert- to 't-', etc., and 'n-' is basically omitted.

Chiral Broensted Acid Derivative

Examples of a chiral Broensted acid derivative that can be employed in the method of asymmetric synthesis of the present invention include a chiral binaphthol-phosphoric acid derivative represented by formula (1) above, that is, an R-form binaphthol-phosphoric acid derivative or an S-form binaphthol-phosphoric acid derivative. That is, formula (1) denotes the R-form or the S-form. This derivative can be synthesized from R-form or S-form 1,1'-binaphthyl-2,2'-diol. Formula (1) can be synthesized by referring to a synthetic method described in, for example, JP-A-47-30617, JP-A-2000-336097, or U.S. Pat. No. 3,848,030. Formula (3) can also be synthesized by referring to these publications.

The synthesis of formula (1) involves, for example, protecting hydroxyl groups of R-form or S-form 1,1'-binaphthyl-2,2'-diol, then producing a 3-position, 3'-position, 6-position, and/or 6'-position halogen derivative, then introducing a substituent by a cross-coupling reaction, etc., and carrying out a phosphorylation by reaction with phosphorus oxychloride, etc. As the halogen of this halogen derivative, a chlorine atom, a bromine atom, or an iodine atom is preferable, and a bromine atom or an iodine atom is more preferable.

The position of the halogen derivative at which the halogen atom is bonded is, for example, the 3-position, 3,3'-positions, 6-position, 3,6'-positions, 6,6'-positions, 3,3',6-positions, 3,6,6'-positions, or 3,3',6,6'-positions, preferably the 3,3'-positions, 3,6'-positions, 6,6'-positions, 3,3',6-positions, or 3,3',6,6'-positions, and more preferably the 3,3'-positions, 3,3',6-positions, or 3,3',6,6'-positions. These bonding positions for the halogen atom also apply to the bonding positions of the substituents in formula (1). Furthermore, these bonding positions also basically apply to the bonding positions of the substituents in formula (3).

Substituents of Formula (1)

$R_1$, $R_2$, $R_3$, and $R_4$ of formula (1) may independently be hydrogen atoms, not all of $R_1$, $R_2$, $R_3$, and $R_4$ are hydrogen atoms, and it is not preferable for $R_1$ and/or $R_2$ to be hydrogen atoms. From this, $R_1$, $R_2$, $R_3$, and $R_4$ of formula (1) preferably may independently denote a hydrogen atom (not all of $R_1$, $R_2$, $R_3$, and $R_4$ are hydrogen atoms); a halogen atom; a nitro group; a monohalogenomethyl group; a dihalogenomethyl group; a trihalogenomethyl group; a nitrile group; a formyl group; —COA$_1$; —COOA$_2$; an optionally branched alkyl group having 1 to 20 carbons; an optionally branched alkenyl group having 3 to 20 carbons; an optionally branched alkoxy group having 1 to 20 carbons; an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —COA$_1$, —COOA$_2$, an optionally branched alkyl group having 1 to 10 carbons, an optionally branched alkenyl group having 1 to 18 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —COA$_1$, —COOA$_2$, and an optionally branched alkyl group having 1 to 20 carbons; a cycloalkyl group having 3 to 8 carbons; or formula (2) below.

Examples of the halogen atom bonded to $R_1$, $R_2$, $R_3$, and/or $R_4$ of formula (1) include a fluorine atom, a chlorine atom, a bromine atom, or an iodine atom, a plurality of types may be bonded simultaneously, and it is preferably a fluorine atom, a chlorine atom, or a bromine atom, and more preferably a chlorine atom or a bromine atom.

Examples of the halogen atom of the monohalogenomethyl group, the dihalogenomethyl group, or the trihalogenomethyl group bonded to $R_1$, $R_2$, $R_3$, and/or $R_4$ of formula (1) include a fluorine atom, a chlorine atom, a bromine atom, or an iodine atom, and it is preferably a fluorine atom, a chlorine atom, or a bromine atom, and more preferably a fluorine atom or a chlorine atom. Those having many halogen atoms bonded thereto are preferable. That is, a trifluoromethyl group or a trichloromethyl group are preferable.

$A_1$ of the —$COA_1$ bonded to $R_1$, $R_2$, $R_3$, and/or $R_4$ of formula (1) denotes an optionally branched alkyl group having 1 to 6 carbons, and is preferably a methyl group or an ethyl group, and more preferably a methyl group.

$A_2$ of the —$COOA_2$ bonded to $R_1$, $R_2$, $R_3$, and/or $R_4$ of formula (1) denotes an optionally branched alkyl group having 1 to 6 carbons, and is preferably a methyl group, an ethyl group, or a propyl group, and more preferably an ethyl group.

The optionally branched alkyl group having 1 to 20 carbons bonded to $R_1$, $R_2$, $R_3$, and/or $R_4$ of formula (1) preferably has 2 to 18 carbons, and more preferably 4 to 16 carbons. Specific examples thereof include a methyl group, an ethyl group, a propyl group, an i-propyl group, a butyl group, an i-butyl group, a t-butyl group, a pentyl group, an i-pentyl group, a hexyl group, an i-hexyl group, an octyl group, an i-octyl group, a nonyl group, a decyl group, a dodecyl group, a tetradecyl group, and a hexadecyl group. It is preferably a t-butyl group, a pentyl group, a hexyl group, or an octyl group.

The optionally branched alkenyl group having 3 to 20 carbons bonded to $R_1$, $R_2$, $R_3$, and/or $R_4$ of formula (1) preferably has 3 to 18 carbons, and more preferably 4 to 16 carbons. Specific examples thereof include a butenyl group, a pentenyl group, a hexenyl group, a heptenyl group, an octenyl group, a nonenyl group, a decenyl group, a dodecenyl group, a tetradecenyl group, and a hexadecenyl group. It is preferably a butenyl group, a pentenyl group, a hexenyl group, a heptenyl group, or an octenyl group.

The optionally branched alkoxy group having 1 to 20 carbons bonded to $R_1$, $R_2$, $R_3$, and/or $R_4$ of formula (1) preferably has 1 to 18 carbons, and more preferably 4 to 16 carbons. Specific examples thereof include a methoxy group, an ethoxy group, a propoxy group, a butoxy group, a pentyloxy group, an i-pentyloxy group, a hexyloxy group, an i-hexyloxy group, an octyloxy group, an i-octyloxy group, a nonyloxy group, a decyloxy group, a dodecyloxy group, a tetradecyloxy group, and a hexadecyloxy group. It is preferably a butoxy group, a pentyloxy group, a hexyloxy group, or an octyloxy group.

Examples of the aryl group bonded to $R_1$, $R_2$, $R_3$, and/or $R_4$ of formula (1) include a phenyl group, a 1-naphthyl group, a 2-naphthyl group, a phenanthryl group; and an anthryl group, and it is preferably a phenyl group, a 1-naphthyl group, or 2-naphthyl group.

Examples of $R_1$, $R_2$, $R_3$, and/or $R_4$ of formula (1) include an aryl group mono- or di-substituted with an aryl group. Examples of the former aryl group include a phenyl group, a naphthyl group, a phenanthryl group, and an anthryl group, and it is preferably a phenyl group or a naphthyl group; examples of the aryl group bonded to the aryl group include a phenyl group, a naphthyl group, a phenanthryl group, and an anthryl group, and it is preferably a phenyl group or a naphthyl group.

Specific examples thereof include a biphenyl group, a naphthylphenyl group, a phenylnaphthyl group, and a naphthylnaphthyl group.

Examples of $R_1$, $R_2$, $R_3$, and/or $R_4$ of formula (1) include an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), —$COOA_2$ ($A_2$ denotes an optionally branched alkyl group having 1 to 6 carbons), an optionally branched alkyl group having 1 to 10 carbons, an optionally branched alkenyl group having 1 to 10 carbons, and an optionally branched alkoxy group having 1 to 20 carbons.

The alkyl group bonded to the aryl group preferably has 1 to 10 carbons, and more preferably 1 to 6 carbons. Specific examples thereof include a methyl group, an ethyl group, a propyl group, and a butyl group. Examples of this aryl group include a tolyl group, a xylyl group, a mesityl group, a methylnaphthyl group, a dimethylnaphthyl group, and a methylanthryl group. It is preferably a tolyl group, a xylyl group, a mesityl group, or a methylnaphthyl group.

The alkenyl group bonded to the aryl group preferably has 3 to 18 carbons, and more preferably 4 to 16 carbons. Specific examples thereof include a butenyl group, a pentenyl group, a hexenyl group, a heptenyl group, an octenyl group, a nonenyl group, a decenyl group, a dodecenyl group, a tetradecenyl group, and a hexadecenyl group. It is preferably a butenyl group, a pentenyl group, a hexenyl group, a heptenyl group, or an octenyl group.

The alkoxy group bonded to the aryl group preferably has 1 to 12 carbons, and more preferably 1 to 6 carbons. Specific examples thereof include a methoxy group, an ethoxy group, a propoxy group, an i-propoxy group, a butoxy group, an i-butoxy group, a t-butoxy group, a pentyloxy group, an i-pentyloxy group, a hexyloxy group, and an i-hexyloxy group. It is preferably a methoxy group, an ethoxy group, or a propoxy group.

The substituent bonded to the aryl group is mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), and —$COOA_2$ ($A_2$ denotes an optionally branched alkyl group having 1 to 6 carbons), and is preferably mono- to tetra-substituted with at least one type selected from the group consisting of a nitro group, a halogen atom, a monohalogenomethyl group, a dihalogenomethyl group, a trihalogenomethyl group, and a nitrile group. Specific examples of the aryl group include derivatives of a phenyl group to which is bonded a p-nitrophenyl group, a m-nitrophenyl group, an o-nitrophenyl group, a 2,4-dinitrophenyl group, a p-fluorophenyl group, a m-fluorophenyl group, an o-fluorophenyl group, a 3,5-difluorophenyl group, a 3,4,5-trifluorophenyl group, a 2,4,6-trifluorophenyl group, a p-chlorophenyl group, a m-chlorophenyl group, an o-chlorophenyl group, a 3,5-dichlorophenyl group, a 3,4,5-trichlorophenyl group, a 2,4,6-trichlorophenyl group, a p-bromophenyl group, a m-bromophenyl group, an o-bromophenyl group, a 3,5-dibromophenyl group, a p-trifluoromethylphenyl group, a m-trifluoromethylphenyl group, an o-trifluoromethylphenyl group, a p-trichloromethylphenyl group, a m-trichloromethylphenyl group, an o-trichloromethylphenyl group, a 3,5-di(trifluoromethyl)phenyl group, a 3,5-di(trichloromethyl)phenyl group, a p-cyanophenyl group, a m-cyanophenyl group, an o-cyanophenyl group, etc. Furthermore, with regard to a 1-naphthyl group and a 2-naphthyl group, those having the same substituents as above can be cited as examples.

Examples of $R_1$, $R_2$, $R_3$, and/or $R_4$ of formula (1) include an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), —$COOA_2$ ($A_2$ denotes an optionally branched alkyl group having 1 to 6 carbons), and an optionally branched alkyl group having 1 to 20 carbons.

As the aryl group that may be mono- to tetra-substituted, an aryl group having the above-mentioned substituent can be used, and preferred examples are the same as above. Among the aryl groups mono- or di-substituted with the aryl group having the substituent, a mono-substituted aryl group is preferable.

Preferred examples of the cycloalkyl group having 3 to 8 carbons in $R_1$, $R_2$, $R_3$, and/or $R_4$ of formula (1) include a cyclobutyl group, a cyclopentyl group, a cyclohexyl group, and a cyclooctyl group. It is preferably a cyclopentyl group or a cyclohexyl group.

Examples of formula (2) denoted by $R_1$, $R_2$, $R_3$, and/or $R_4$ of formula (1) include a triphenylsilyl group, a trimethylsilyl group, a dimethylethylsilyl group, a triethylsilyl group, a triisopropylsilyl group, a t-butyldimethylsilyl group, a t-butyldiphenylsilyl group, and a diphenylmethylsilyl group. It is preferably a triphenylsilyl group, a trimethylsilyl group, or a diphenylmethylsilyl group.

Although examples of $R_1$, $R_2$, $R_3$, and $R_4$ in formula (1) are described above, it is preferable for the chiral Broensted acid to have an electron-attracting group such as a nitro group or a trifluoromethyl group bonded thereto for use in a method of asymmetric synthesis of the present invention. Examples of such an electron-attracting group include a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), and —$COOA_2$ ($A_2$ denotes an optionally branched alkyl group having 1 to 6 carbons), and preferred examples thereof include a nitro group, a halogen atom, a monohalogenomethyl group, a dihalogenomethyl group, a trihalogenomethyl group, a nitrile group, and a formyl group. Examples of the halogen atom of the monohalogenomethyl group, the dihalogenomethyl group, or the trihalogenomethyl group include a fluorine atom, a chlorine atom, a bromine atom, and an iodine atom, and it is preferably a fluorine atom, a chlorine atom, or a bromine atom, and more preferably a fluorine atom or a chlorine atom. Furthermore, $A_1$ of —$COA_1$ denotes an optionally branched alkyl group having 1 to 6 carbons, and is preferably a methyl group or an ethyl group, and more preferably a methyl group. Furthermore, —$COOA_2$ may be an ester group to which an alkyl group having 1 to 6 carbons is bonded, and is preferably an ethyl ester group.

$R_1$, $R_2$, $R_3$, and $R_4$ of formula (1) in the present invention are preferably an aryl group to which an electron-attracting group is bonded, more preferably a phenyl group to which an electron-attracting group is bonded, and particularly preferably a phenyl group to which a nitro group, a halogen atom, a monohalogenomethyl group, a dihalogenomethyl group, a trihalogenomethyl group, a nitrile group, or a formyl group is bonded. A plurality of these electron-attracting groups may be bonded. It is preferable that an aryl group having electron-attracting groups such as a nitro group or a trifluoromethyl group is bonded to $R_1$ and $R_2$. In addition, the electron-attracting group bonded to the aryl group is preferably bonded at a position in which electron attracting properties are exhibited.

Those to which a substituent is bonded in formula (1) are $R_1$, $R_2$, $R_3$, and $R_4$, and $R_1$ and $R_2$ are preferable.

As $R_1$ and $R_2$ of formula (3) in the present invention, those cited as examples in the explanation of formula (1) can be used.

As the asymmetric synthesis catalyst in the present invention, it is preferable to use a compound represented by formula (1).

A chiral Broensted acid represented by formula (1) or formula (3) used in the asymmetric synthesis may be in the form of a salt as long as it can be used as an acid catalyst.

Examples of the chiral binaphthol-phosphoric acid derivative used in the present invention are listed below. The compounds illustrated below are the R-form or the S-form, but their notation is omitted. That is, (R)-3,3'-bis(4-nitrophenyl)-1,1'-binaphthyl-2,2'-diylphosphoric acid and (S)-3,3'-bis(4-nitrophenyl)-1,1'-binaphthyl-2,2'-diylphosphoric acid are expressed as 3,3'-bis(4-nitrophenyl)-1,1'-binaphthyl-2,2'-diylphosphoric acid.

Examples of the chiral binaphthol-phosphoric acid derivative include 3,3'-dimethyl-1,1'-binaphthyl-2,2'-diylphosphoric acid, 3,3'-diethyl-1,1'-binaphthyl-2,2'-diylphosphoric acid, 3,3'-dipropyl-1,1'-binaphthyl-2,2'-diylphosphoric acid, 3,3'-diisopropyl-1,1'-binaphthyl-2,2'-diylphosphoric acid, 3,3'-dibutyl-1,1'-binaphthyl-2,2'-diylphosphoric acid, 3,3'-di-t-butyl-1,1'-binaphthyl-2,2'-diylphosphoric acid, 3,3'-dipentyl-1,1'-binaphthyl-2,2'-diylphosphoric acid, 3,3'-dihexyl-1,1'-binaphthyl-2,2'-diylphosphoric acid, 3,3'-dicyclohexyl-1,1'-binaphthyl-2,2'-diylphosphoric acid, 3,3'-diheptyl-1,1'-binaphthyl-2,2'-diylphosphoric acid, 3,3'-dioctyl-1,1'-binaphthyl-2,2'-diylphosphoric acid, 3,3'-dinonyl-1,1'-binaphthyl-2,2'-diylphosphoric acid, 3,3'-didecyl-1,1'-binaphthyl-2,2'-diylphosphoric acid, 3,3'-diphenyl-1,1'-binaphthyl-2,2'-diylphosphoric acid, 3,3'-bis(4-methylphenyl)-1,1'-binaphthyl-2,2'-diylphosphoric acid, 3,3'-bis(2,6-dimethylphenyl)-1,1'-binaphthyl-2,2'-diylphosphoric acid, 3,3'-diethynyl-1,1'-binaphthyl-2,2'-diylphosphoric acid, 6,6'-diethenyl-1,1'-binaphthyl-2,2'-diylphosphoric acid, 3,3'-dioctenyl-1,1'-binaphthyl-2,2'-diylphosphoric acid, 6,6'-diethynyl-1,1'-binaphthyl-2,2'-diylphosphoric acid, 3,3'-diethynyl-1,1'-binaphthyl-2,2'-diylphosphoric acid, 6,6'-diethenyl-1,1'-binaphthyl-2,2'-diylphosphoric acid, 3,3'-bis(triphenylsilyl)-1,1'-binaphthyl-2,2'-diylphosphoric acid, 3,3'-bis(mesityl)-1,1'-binaphthyl-2,2'-diylphosphoric acid, 3,3'-bis(4-biphenyl)-1,1'-binaphthyl-2,2'-diylphosphoric acid, 3,3'-bis(2-naphthyl)-1,1'-binaphthyl-2,2'-diylphosphoric acid, 3,3'-bis(2',4',6'-trimethylbiphenyl-4-yl))-1,1'-binaphthyl-2,2'-diylphosphoric acid, 3,3'-bis(4-naphthalen-2-yl-phenyl)-1,1'-binaphthyl-2,2'-diylphosphoric acid, 3,3'-bis(4-methoxyphenyl)-1,1'-binaphthyl-2,2'-diylphosphoric acid, 3,3'-bis(4-trifluoromethylphenyl)-1,1'-binaphthyl-2,2'-diylphosphoric acid, 3,3'-bis[3,5-di(trifluoromethyl)phenyl]-1,1'-binaphthyl-2,2'-diylphosphoric acid, 3,3'-bis(4-trichloromethylphenyl)-1,1'-binaphthyl-2,2'-diylphosphoric acid, 3,3'-bis[3,5-di(trichloromethyl)phenyl]-1,1'-binaphthyl-2,2'-diylphosphoric acid, 3,3'-bis(4-nitrophenyl)-1,1'-binaphthyl-2,2'-diylphosphoric acid, 3,3'-bis(3,5-dinitrophenyl)-1,1'-binaphthyl-2,2'-diylphosphoric acid, 3,3'-bis(4-cyanophenyl)-1,1'-binaphthyl-2,2'-diylphosphoric acid, and 6,6'-dibromo-3,3'-diphenyl-1,1'-binaphthyl-2,2'-diylphosphoric acid.

The substituents at the 3,3'-positions of the compounds represented by formula (1) can be applied to those of formula (3). Examples thereof include 3,3'-bis(4-trifluoromethylphenyl)-5,5',6,6',7,7',8,8'-octahydro-1,1'-binaphthyl-2,2'-diylphosphoric acid, 3,3'-bis(4-trichloromethylphenyl)-5,5',6,6',7,7',8,8'-octahydro-1,1'-binaphthyl-2,2'-diylphosphoric acid, 3,3'-bis[3,5-di(trifluoromethyl)phenyl]-5,5',6,6',7,7',8,8'-octahydro-1,1'-binaphthyl-2,2'-diylphosphoric acid, 3,3'-bis[3,5-di(trichloromethyl)phenyl]-5,5',6,6',7,7',8,8'-octahydro-1,1'-binaphthyl-2,2'-diylphosphoric acid, 3,3'-bis(4- nitrophenyl)-5,5',6,6',7,7',8,8'-octahydro-1,1'-binaphthyl-2, 2'-diylphosphoric acid, and 3,3'-bis(3,5-dinitrophenyl)-5,5', 6,6',7,7',8,8'-octahydro-1,1'-binaphthyl-2,2'-diylphosphoric acid.

Example of Application to Asymmetric Reaction

The present invention can be applied to a synthetic reaction using a Broensted acid as a catalyst. That is, by use of a chiral Broensted acid as a catalyst, a chiral compound can be obtained as a reaction product. Examples of the reaction to which the present invention can be applied include an asymmetric Mannich reaction, an asymmetric aza Diels-Alder reaction, an asymmetric allylation reaction, an asymmetric hydrophosphorylation reaction, an asymmetric Strecker reaction, and an asymmetric aminoalkylation reaction of an aromatic compound. However, the reaction examples are not limited to the above as long as a chiral compound can be obtained using, as a catalyst, a chiral binaphthol-phosphoric acid derivative of formula (1) or formula (3).

The absolute configuration of a product obtained by the reaction of the present invention depends on the absolute configuration of the chiral Broensted acid. That is, when an R-form Broensted acid is used, a product having an asymmetric carbon corresponding thereto is given, and when an S-form Broensted acid is used, a product having an asymmetric carbon corresponding thereto is given. When an R-form of formula (1) is used, a product having an asymmetric carbon corresponding thereto is given, and when an S-form of formula (1) is used, a product having an asymmetric carbon corresponding thereto is given. With regard to the absolute configuration of the product, the R-form Broensted acids do not always give an R-form, and the absolute configuration of the product depends on the starting material. This also applies to formula (3).

When carrying out an asymmetric synthetic reaction using the catalyst of the present invention, for the purpose of removing water from a reaction system, various types of zeolite such as A-type zeolite represented by molecular sieves 3A, 4A, and 5A, molecular sieve 13X, Y-type, or L-type may be used as necessary.

Asymmetric Mannich Reaction

In an example of the asymmetric Mannich reaction that is carried out by applying the present invention, an amino compound represented by formula (6) below is obtained from an enol derivative represented by formula (4) below and an imine derivative represented by formula (5) below.

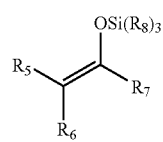

(4)

$R_5$ of formula (4) denotes a hydrogen atom, an optionally branched alkyl group having 1 to 6 carbons, or an aryl group that may have an alkyl group having 1 to 6 carbons, $R_6$ denotes a hydrogen atom or an optionally branched alkyl group having 1 to 6 carbons, $R_7$ denotes an optionally branched alkyl group having 1 to 6 carbons or an optionally branched alkoxy group having 1 to 6 carbons, and $R_8$ may each be independent, and denotes an optionally branched alkyl group having 1 to 6 carbons, a phenyl group, or a phenyl group mono- to tetra-substituted with an optionally branched alkyl group having 1 to 6 carbons.

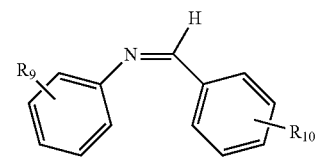

(5)

$R_9$ of formula (5) denotes a hydrogen atom, a hydroxyl group, a halogen atom, an optionally branched alkyl group having 1 to 6 carbons, or an optionally branched alkoxy group having 1 to 6 carbons, and $R_{10}$ denotes a hydrogen atom, a halogen atom, an optionally branched alkyl group having 1 to 6 carbons, or an optionally branched alkoxy group having 1 to 6 carbons.

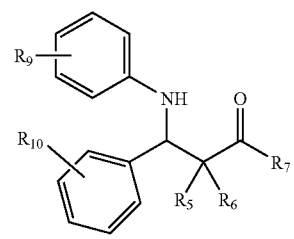

(6)

$R_5$ to $R_7$ of formula (6) are the same as those of formula (4), and $R_9$ and $R_{10}$ are the same as those of formula (5).

The amount of formula (1) or formula (3) used when the present invention is applied to the asymmetric Mannich reaction may be in any proportion, but use of too excessive an amount is not economical, and too little an amount might not cause the asymmetric synthesis reaction to progress, which is undesirable. From this, the proportion of the chiral Broensted acid of formula (1) or formula (3) used when the present invention is applied to the asymmetric Mannich reaction is equal to or greater than 0.01 mol % of the imine derivative represented by formula (5) and is equal to or less than 90 mol %. From this, the proportion of formula (1) or formula (3) used is preferably 0.01 to 90 mol %, more preferably 0.1 to 60 mol %, particularly preferably 1 to 50 mol %, and yet more particularly preferably 3 to 30 mol %.

When the present invention is applied to other asymmetric syntheses, the proportion of the chiral Broensted acid may be the same proportion as employed in the asymmetric Mannich reaction.

With regard to an imine that can be used in the asymmetric Mannich reaction in the present invention, any type of imine may be employed, and specific examples are those of formula (5).

More specific examples of the imine compound include a compound of formula (5) in which $R_9$ is a hydroxyl group and $R_{10}$ is a hydrogen atom.

With regard to an enol that can be used in the asymmetric Mannich reaction in the present invention, any type of enol can be employed, and specific examples are those of formula (4).

$R_5$ of formula (4) is a hydrogen atom, an optionally branched alkyl group having 1 to 6 carbons, or an aryl group that may have an alkyl group having 1 to 6 carbons, is preferably an alkyl group having 1 to 6 carbons or an aryl group, and is more preferably a methyl group or an ethyl group.

$R_6$ of formula (4) is a hydrogen atom or an optionally branched alkyl group having 1 to 6 carbons, preferably an alkyl group having 1 to 6 carbons, and more preferably a methyl group or an ethyl group.

$R_7$ of formula (4) is an optionally branched alkoxy group having 1 to 6 carbons or an optionally branched alkyl group having 1 to 6 carbons, is preferably an optionally branched alkyl group having 1 to 6 carbons, and is more preferably a methyl group, an ethyl group, or a propyl group.

The $R_8$ groups of formula (4) may be different from each other, and are optionally branched alkyl groups having 1 to 4 carbons or phenyl groups, preferably optionally branched alkyl groups having 1 to 4 carbons, which may be different from each other, and more preferably optionally branched alkyl groups having 1 to 3 carbons.

Specific examples of the enol compound include one represented by formula (4) in which $R_5$ and $R_6$ are methyl groups, $R_7$ is a methoxy group, and the $R_8$ groups are methyl groups, one in which $R_5$ and $R_6$ are methyl groups, $R_7$ is a methoxy group, and the $R_8$ groups are t-butyl and methyl groups, one in which $R_5$ and $R_6$ are methyl groups, $R_7$ is an i-propoxy group, and the $R_8$ groups are methyl groups, and one in which $R_5$ and $R_6$ are hydrogen atoms, $R_7$ is a methoxy group, and the $R_8$ groups are methyl groups.

Formula (4) can be obtained from a carboxylic acid ester, a ketone, or an aldehyde and a silyl chloride represented by formula (7) below, etc.

$$(R_8)_3SiCl \qquad (7)$$

$R_8$ of formula (7) is the same as $R_8$ of formula (4).

For example, 1-cyclohexenyloxy-[((1-naphthyl)phenyl)methyl]dimethylsilane, which is a silyl enol ether form of cyclohexanone, may be formed by treating cyclohexanone with lithium diisopropylamide at low temperature (e.g. −78° C.) so as to generate a lithium enolate, and capturing this with [((1-naphthyl)phenyl)methyl]dimethylsilyl chloride. By the same method, a ketone having an active hydrogen such as acetone or benzophenone may be derivatized to the corresponding silyl enol ether. Furthermore, a silyl ketene acetal form of benzyl acetate may be formed by treating benzyl acetate with lithium diisopropylamide at low temperature (e.g. −78° C.) so as to generate a lithium enolate, and capturing this with [((1-naphthyl)phenyl)methyl]dimethylsilyl chloride. By the same method, a carboxylic acid ester having an active hydrogen may be derivatized to the corresponding silyl ketene acetal.

With regard to ketones that can be employed in order to obtain formula (4) of the present invention, most ketones can be employed, and examples thereof include acetophenone, (4-methylphenyl)acetophenone, (3-methylphenyl)acetophenone, (2-methylphenyl)acetophenone, (4-ethylphenyl)acetophenone, (3-ethylphenyl)acetophenone, (2-ethylphenyl)acetophenone, (4-i-propylphenyl)acetophenone, (3-i-propylphenyl)acetophenone, (2-i-propylphenyl)acetophenone, 1-phenylpropan-1-one, 1-(4-methylphenyl)propan-1-one, 1-(3-methylphenyl)propan-1-one, 1-(2-methylphenyl)propan-1-one, 1-phenyl-butan-1-one, 1-(4-methylphenyl)-butan-1-one, 1-(3-methylphenyl)-butan-1-one, 1-(2-methylphenyl)-butan-1-one, 1-phenyl-2-methylpropan-1-one, 1-(4-phenyl)-2-methylpropan-1-one, 1-(3-phenyl)-2-methylpropan-1-one, 1-(2-phenyl)-2-methylpropan-1-one, 1-phenyl-pentan-1-one, 1-phenyl-hexan-1-one, 1-phenyl-heptan-1-one, 1-phenyl-octan-1-one, 1-phenyl-nonan-1-one, 1-phenyl-decan-1-one, 1-phenyl-undecan-1-one, 1-phenyl-dodecan-1-one, 1-phenyl-tridecan-1-one, 1-phenyl-tetradecan-1-one, 1-phenyl-pentadecan-1-one, 1-phenyl-hexadecan-1-one, methyl t-butyl ketone, ethyl glyoxylate, ethyl phenyl glyoxylate, methyl phenyl glyoxylate, ethyl i-propyl glyoxylate, ethyl phenylethenyl glyoxylate, and ethyl cyclohexyl glyoxylate.

With regard to aldehydes that can be employed in order to obtain formula (4) of the present invention, most aldehydes can be employed, and examples thereof include ethyl formate, methoxycarbonyl aldehyde, acetaldehyde, propionaldehyde, butanal, isobutanal, pentanal, acrolein, crotonaldehyde, cyclohexyl aldehyde, benzaldehyde, 4-methoxybenzaldehyde, 4-methylbenzaldehyde, 3,5-dimethylbenzaldehyde, 4-phenylbenzaldehyde, 4-chlorobenzaldehyde, 4-nitrobenzaldehyde, naphthyl-2-aldehyde, 2-furfural, cinnamaldehyde, 3-phenylpropanal, and 2-benzyloxyacetaldehyde and, furthermore, as compounds analogous to aldehydes, a benzylimine, a phenylthioamide, etc. can be cited.

When the method of asymmetric synthesis of the present invention is applied to the asymmetric Mannich reaction, an imine represented by formula (5) and a ketone or an enol represented by formula (4) are often reacted in equimolar amounts, but the ketone or the enol may be used at 0.1 to 10 moles per mole of the imine, preferably 1 to 5 moles, and more preferably 1 to 4 moles.

When the method of asymmetric synthesis of the present invention is applied to the asymmetric Mannich reaction, most solvents may be used as long as they are inert to the reaction. Specific examples thereof include halogenated solvents such as carbon tetrachloride, chloroform, dichloromethane, 1,2-dichloroethane, 1,1,1-trichloroethane, and 1,1,2-trichloroethane, ether solvents such as diethyl ether and tetrahydrofuran, and aromatic solvents such as toluene, xylene, ethylbenzene, isopropylbenzene, and mesitylene, and it is preferable to use an aromatic solvent.

When the method of asymmetric synthesis of the present invention is applied to the asymmetric Mannich reaction, the reaction temperature depends on the compound used in the reaction, but it can usually be carried out in the range of −100° C. to 50° C., preferably −80° C. to 0° C., and more preferably −78° C. to −40° C.

When the method of asymmetric synthesis of the present invention is applied to the asymmetric Mannich reaction, the concentrations of formula (4) and formula (5) used in the reaction are not particularly limited as long as they can be dissolved in a solvent. Even when the concentration is too high to be dissolved in a solvent, as long as the reaction is not inhibited the present method of asymmetric synthesis can be employed. It is usually in the range of 0.1 mass % to 50 mass % relative to the solvent.

When the method of asymmetric synthesis of the present invention is applied to the asymmetric Mannich reaction, the reaction time depends on the type of compound and the type of chiral Broensted acid catalyst used in the reaction, but it may usually be carried out in 1 to 96 hours.

As a posttreatment after the method of asymmetric synthesis of the present invention is applied to the asymmetric Mannich reaction, a standard purification method can be used. Specifically, there is a method in which an appropriate amount of an aqueous solution of sodium hydrogen carbonate is added to a reaction mixture, it is then extracted with ethyl acetate, dried over anhydrous sodium sulfate, and filtered, and the filtrate is concentrated to give a product, etc. When purifying this product, a standard method such as preparative silica gel thin-layer chromatography, column chromatography, distillation, or recrystallization can be used.

The asymmetric Mannich reaction to which the present invention is applied is explained above, but as described above the present invention can also be applied to an asymmetric aza Diels-Alder reaction, an asymmetric allylation reaction, an asymmetric hydrophosphorylation reaction, an asymmetric Strecker reaction, an aminoalkylation reaction of an asymmetric aromatic compound, etc.

When the present invention is applied to these asymmetric reactions, the conditions for each reaction may be determined by modifying as necessary the conditions described for the asymmetric Mannich reaction. That is, the conditions described for the asymmetric Mannich reaction may be employed while taking into consideration the amount of acid catalyst in each asymmetric reaction.

Asymmetric aza Diels-Alder Reaction

Examples of the asymmetric aza Diels-Alder reaction to which the present invention is applied include one in which formula (9) below is obtained from formula (5) and formula (8) below.

With regard to formula (5) used in the asymmetric aza Diels-Alder reaction, those that can be employed in the asymmetric Mannich reaction can be used.

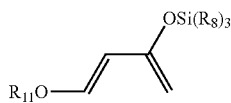
(8)

$R_8$ of formula (8) may be the same as $R_8$ of formula (4), and $R_{11}$ denotes an optionally branched alkyl group having 1 to 6 carbons. It is preferably a methyl group or an ethyl group.

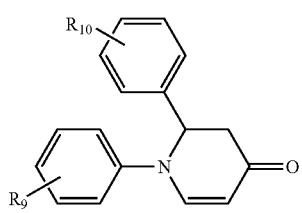
(9)

$R_9$ and $R_{10}$ of formula (9) are the same as those of formula (5).

Asymmetric Allylation Reaction

Examples of the asymmetric allylation reaction to which the present invention is applied include one in which formula (12) below is obtained from formula (10) below and formula (11) below.

(10)

$R_{12}$ of formula (10) denotes an optionally branched alkyl group having 1 to 6 carbons or an aryl group having a substituent, and $R_{13}$ denotes an aryl group that may have a substituent such as a hydroxyl group.

(11)

B1 of formula (11) denotes a trialkylstannyl group or a trialkylsilyl group, and this alkyl group is an optionally branched one having 1 to 6 carbons.

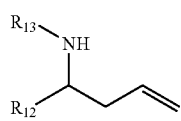
(12)

$R_{12}$ and $R_{13}$ of formula (12) are the same as those of formula (10).

$R_{12}$ of formula (10) denotes an optionally branched alkyl group having 1 to 6 carbons or an aryl group having a substituent, and preferred examples thereof include a methyl group, an ethyl group, and a phenyl group. $R_{13}$ denotes an aryl group that may have a substituent such as a hydroxyl group; preferred examples thereof include a phenyl group and a phenyl group having a hydroxyl group, and it is particularly preferably a 2-hydroxyphenyl group.

B1 of formula (11) denotes a trialkylstannyl group or a trialkylsilyl group; this alkyl group is an optionally branched one having 1 to 6 carbons, and is preferably a methyl group or an ethyl group.

$R_{12}$ and $R_{13}$ of formula (12) are the same as those of formula (10).

Asymmetric Hydrophosphorylation Reaction

Examples of the asymmetric hydrophosphorylation reaction to which the present invention is applied include one in which formula (14) is obtained from formula (10) and formula (13) below.

(13)

$R_{14}$ of formula (13) denotes an optionally branched alkyl group having 1 to 6 carbons.

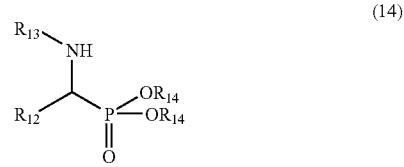
(14)

$R_{12}$ and $R_{13}$ of formula (14) are the same as those of formula (10), and $R_{14}$ is the same as that of formula (13).

$R_{14}$ of formula (13) denotes an optionally branched alkyl group having 1 to 6 carbons, and is preferably a methyl group or an ethyl group.

$R_{12}$ and $R_{13}$ of formula (14) are the same as those of formula (10), and $R_{14}$ is the same as that of formula (13).

Asymmetric Strecker Reaction

Examples of the asymmetric Strecker reaction to which the present invention is applied include one in which formula (16) is obtained from formula (10) and formula (15) below.

(15)

B2 of formula (15) denotes a hydrogen atom, a trialkylstannyl group, or a trialkylsilyl group, and this alkyl group is an optionally branched one having 1 to 6 carbons.

(16)

$R_{12}$ and $R_{13}$ of formula (16) are the same as those of formula (10).

B2 of formula (15) denotes a hydrogen atom, a trialkylstannyl group, or a trialkylsilyl group; this alkyl group is an optionally branched one having 1 to 6 carbons, and is preferably a methyl group or an ethyl group.

$R_{12}$ and $R_{13}$ of formula (16) are the same as those of formula (10).

Asymmetric Aminoalkylation Reaction of Aromatic Compound

Examples of the asymmetric aminoalkylation reaction of an aromatic compound to which the present invention is applied include one in which formula (18) is obtained from formula (10) and formula (17) below.

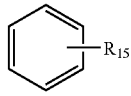
(17)

With regard to $R_{15}$ of formula (17), a plurality thereof may be bonded, and when a plurality thereof are bonded, they may be different from each other. $R_{15}$ denotes a hydroxyl group, a halogen atom, an optionally branched alkyl group having 1 to 6 carbons, or an optionally branched alkoxy group having 1 to 6 carbons.

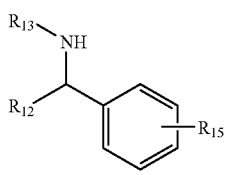
(18)

$R_{12}$ and $R_{13}$ of formula (18) are the same as those of formula (10), and $R_{15}$ is the same as that of formula (17).

With regard to $R_{15}$ of formula (17), a plurality thereof may be bonded, and when a plurality thereof are bonded, they may be different from each other. $R_{15}$ denotes a hydroxyl group, a halogen atom, an optionally branched alkyl group having 1 to 6 carbons, or an optionally branched alkoxy group having 1 to 6 carbons. The optionally branched alkyl group having 1 to 6 carbons is preferably a methyl group, an ethyl group, or a propyl group, and the optionally branched alkoxy group having 1 to 6 carbons is preferably a methoxy group or an ethoxy group.

$R_{12}$ and $R_{13}$ of formula (18) are the same as those of formula (10), and $R_{15}$ is the same as that of formula (17).

The present invention may be applied to a synthetic reaction using a Broensted acid as a catalyst, thus giving a chiral compound. Here, since no metal salt or metal complex is used, the burden on the environment is small. Furthermore, with regard to the conditions of the asymmetric synthesis to which the present invention is applied, the conditions of the synthetic reaction using a Broensted acid as a catalyst can be used with hardly any modification.

The chiral compounds obtained by application of the present invention are useful as compounds used in perfumes, pharmaceuticals, agrochemicals, etc. and synthetic intermediates therefor.

In a method of asymmetric synthesis using, as a catalyst, a chiral Broensted acid represented by formula (1), in formula (1), $R_1$, $R_2$, $R_3$, and $R_4$ may be independent of each other, and denote a hydrogen atom ($R_1$, $R_2$, $R_3$, and $R_4$ are not hydrogen atoms simultaneously); an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkyl group having 1 to 20 carbons; a cycloalkyl group having 3 to 8 carbons; or formula (2). $A_1$ denotes an optionally branched alkyl group having 1 to 6 carbons, and $A_2$ denotes an optionally branched alkyl group having 1 to 6 carbons. Furthermore, it is not desirable that a hydrogen atom is bonded as $R_1$ or $R_2$.

In a method of asymmetric synthesis using, as a catalyst, a chiral Broensted acid represented by formula (3), in formula (3), $R_1$ and $R_2$ may be independent of each other, and denote a hydrogen atom ($R_1$ and $R_2$ are not hydrogen atoms simultaneously); an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkyl group having 1 to 20 carbons; a cycloalkyl group having 3 to 8 carbons; or formula (2). $A_1$ denotes an optionally branched alkyl group having 1 to 6 carbons, and $A_2$ denotes an optionally branched alkyl group having 1 to 6 carbons. Furthermore, it is not desirable that a hydrogen atom is bonded as $R_1$ or $R_2$.

In a method of asymmetric synthesis using, as a catalyst, a chiral Broensted acid represented by formula (1), in formula (1), $R_3$ and $R_4$ may be independent of each other, and denote a hydrogen atom, a halogen atom, a nitro group, a monohalogenomethyl group, a dihalogenomethyl group, a trihalogenomethyl group, a nitrile group, a formyl group, —$COA_1$, —$COOA_2$, an optionally branched alkyl group having 1 to 20 carbons, an optionally branched alkenyl group having 3 to 20 carbons, an optionally branched alkoxy group having 1 to 20 carbons, or an aryl group, and $R_1$ and $R_2$ may be independent of each other, and denote an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkyl group having 1 to 20 carbons; a cycloalkyl group having 3 to 8 carbons; or formula (2). $A_1$ denotes an optionally branched alkyl group having 1 to 6 carbons, and $A_2$ denotes an optionally branched alkyl group having 1 to 6 carbons.

In a method of asymmetric synthesis using, as a catalyst, a chiral Broensted acid represented by formula (3), $R_1$ and $R_2$ may be independent of each other, and denote an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkyl group having 1 to 20 carbons; a cycloalkyl group having 3 to 8 carbons; or formula (2). $A_1$ denotes an optionally branched alkyl group having 1 to 6 carbons, and $A_2$ denotes an optionally branched alkyl group having 1 to 6 carbons.

In a method of asymmetric synthesis using, as a catalyst, a chiral Broensted acid represented by formula (1), in formula (1), $R_3$ and $R_4$ may be independent of each other, and denote a hydrogen atom, a halogen atom, a nitro group, a monohalogenomethyl group, a dihalogenomethyl group, a trihalogenomethyl group, a nitrile group, a formyl group, —$COA_1$, —$COOA_2$, or an optionally branched alkoxy group having 1 to 20 carbons, and $R_1$ and $R_2$ may be independent of each other, and denote an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkyl group having 1 to 20 carbons; or formula (2). $A_1$ denotes an optionally branched alkyl group having 1 to 6 carbons, and $A_2$ denotes an optionally branched alkyl group having 1 to 6 carbons.

In a method of asymmetric synthesis using, as a catalyst, a chiral Broensted acid represented by formula (3), $R_1$ and $R_2$ may be independent of each other, and denote an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkyl group having 1 to 20 carbons; or formula (2). $A_1$ denotes an optionally branched alkyl group having 1 to 6 carbons, and $A_2$ denotes an optionally branched alkyl group having 1 to 6 carbons.

In a method of asymmetric synthesis using as a catalyst a chiral Broensted acid represented by formula (1), in formula (1), $R_3$ and $R_4$ may be independent of each other, and denote a hydrogen atom, a halogen atom, a nitro group, an optionally branched alkyl group having 1 to 20 carbons, an optionally branched alkoxy group having 1 to 20 carbons, or an aryl group, and $R_1$ and $R_2$ may be independent of each other, and denote an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, an optionally branched alkyl group having 1 to 10 carbons, an optionally branched alkenyl group having 1 to 10 carbons, and an optionally branched alkoxy group having 1 to 20 carbons; or formula (2). $A_1$ denotes an optionally branched alkyl group having 1 to 6 carbons, and $A_2$ denotes an optionally branched alkyl group having 1 to 6 carbons.

In a method of asymmetric synthesis using, as a catalyst, a chiral Broensted acid represented by formula (3), $R_1$ and $R_2$ may be independent of each other, and denote an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, an optionally branched alkyl group having 1 to 10 carbons, an optionally branched alkenyl group having 1 to 10 carbons, and an optionally branched alkoxy group having 1 to 20 carbons; or formula (2). $A_1$ denotes an optionally branched alkyl group having 1 to 6 carbons, and $A_2$ denotes an optionally branched alkyl group having 1 to 6 carbons.

In a method of asymmetric synthesis using, as a catalyst, a chiral Broensted acid represented by formula (1), in formula (1), $R_3$ and $R_4$ may be independent of each other, and denote a hydrogen atom or a halogen atom, and $R_1$ and $R_2$ may be independent of each other, and denote an aryl group; an aryl group mono- or di-substituted with an aryl group; or an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkoxy group having 1 to 20 carbons. $A_1$ denotes an optionally branched alkyl group having 1 to 6 carbons, and $A_2$ denotes an optionally branched alkyl group having 1 to 6 carbons.

In a method of asymmetric synthesis using, as a catalyst, a chiral Broensted acid represented by formula (3), in formula (1) $R_1$ and $R_2$ may be independent of each other, and denote an aryl group; an aryl group mono- or di-substituted with an aryl group; or an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$, —$COOA_2$, and an optionally branched alkoxy group having 1 to 20 carbons. $A_1$ denotes an optionally branched alkyl group having 1 to 6 carbons, and $A_2$ denotes an optionally branched alkyl group having 1 to 6 carbons.

A method of asymmetric synthesis using a chiral Broensted acid as a catalyst in an aromatic solvent.

A method of asymmetric synthesis using formula (1) or formula (3) as a catalyst in an aromatic solvent.

EXAMPLES

Hereinafter, the present invention will be described specifically by means of Examples, but the invention is not intended to be limited to these Examples. M represents molar concentration (mol/L). As for synthetic operations, the inside of the reaction system was substituted with nitrogen gas, and reagents and solvents were dehydrated before use.

Synthetic Example 1

Synthesis of (R)-2,2'-dimethoxy-1,1'-binaphthyl (GA06)

(R)-1,1'-binaphthyl-2,2'-diol (referred to as (R)-BINOL), methyl iodide, and potassium carbonate were refluxed in acetone for 30 hours to give GA06.

Synthetic Example 2

Synthesis of (R)-3,3'-diiodo-2,2'-dimethoxy-1,1'-binaphthyl (GA12)

Diethyl ether (200 mL) and N,N,N',N'-tetramethylethylenediamine (TMEDA; 26.2 mmol) were put in a three-necked round bottom flask and stirred. n-Butyllithium (n-BuLi; 48.9 mmol) was added dropwise over 20 minutes or more at room temperature. After that, GA06 (19.1 mmol) obtained in Synthetic example 1 was added, which was stirred overnight. The reaction mixture was cooled to −78° C. A solution prepared by dissolving iodine (71.2 mmol) in tetrahydrofuran (24 mL) was added dropwise, and the reaction mixture was stirred for 1 hour. Then, the mixture was warmed to room temperature and stirred for additional 12 hours. The reaction mixture was cooled to 0° C., and then the reaction was quenched by the addition of water and stirring for 2 hours. The solution was extracted with diethyl ether three times. The combined extracts was washed with an aqueous sodium thiosulfate solution and brine, and dried over anhydrous sodium sulfate. After the drying, the extracts was filtered, the filtrate was concentrated and then separated and purified by means of column chromatography to give GA12 (10.6 mmol, yield: 55%).

Rf=0.3 (Hexane:$CH_2Cl_2$=6:1).

$^1$H-NMR (400 MHz,$CDCl_3$) δ=8.53 (s,2H), 7.80 (d,2H, J=7.7 Hz), 7.41 (m,2H), 7.27 (m,2H), 7.07 (d,2H,J=8.6 Hz), 3.42 (s,6H).

Synthetic Example 3

Synthesis of (R)-3,3'-diphenyl-2,2'-dimethoxy-1,1'-binaphthyl (GA03)

GA12 (7.1 mmol) obtained in Synthetic example 2, Nickel (II) acetylacetonate (Ni(ACAC)$_2$, 0.73 mmol) and benzene (40 mL) were put in a three-necked round bottom flask. Phenyl MgBr prepared separately was added dropwise over 10 minutes or more at room temperature, and the reaction mixture was stirred for additional 30 minutes. Then, the mixture was heated and refluxed for 12 hours. The reaction mixture was cooled to 0° C., and then the reaction was quenched by the addition of 1 M hydrochloric acid and stirring for 1 hour. The reaction mixture was extracted with diethyl ether three times. The combined extracts was washed with brine and dried over anhydrous sodium sulfate. After the drying, the extract was filtered, the filtrate was concentrated and then separated and purified by means of column chromatography to give GA03.

Synthetic Example 4

Synthesis of (R)-3,3'-diphenyl-1,1'-binaphthyl-2,2'-diyl hydrogenphosphate (GA04)

GA03 (1.91 mmol) obtained in Synthetic example 3 and pyridine (7.8 mL) were put in a two-necked round bottom flask. To the solution, phosphoryl chloride (2.69 mmol) was added dropwise over 7 minutes at room temperature. The reaction mixture was stirred for additional 2 hours. Then, the reaction mixture was heated and refluxed for 1 hour. The reaction mixture was cooled to room temperature, and distillated water (1.6 mL) was added dropwise. Then, the mixture was heated and refluxed for 1.5 hours and cooled to room temperature. Pyridine was distilled away under a reduced pressure from the mixture. Subsequently, 6 M hydrochloric acid (15 mL) was added dropwise to the mixture and heated and refluxed for additional 2 hours. The reaction mixture was cooled to 0° C. and filtered. The filtrate was washed with water and dried. The crude product was recrystallized in methanol to give GA04.

Synthetic Example 5

Synthesis of (R)-3,3'-dibromo-2,2'-dimethoxy-1,1'-binaphthyl (GA07)

GA06 (12.6 mmol) obtained in Synthetic example 1 and 200 mL of diethyl ether were put in a three-necked round bottom flask, n-BuLi (37.4 mmol) and TMEDA (30 mmol) were added at room temperature, and the reaction mixture was stirred for 3 hours. The reaction mixture was cooled to −78° C. A solution prepared by dissolving bromine (177 mmol) in 50 mL of diethyl ether was added dropwise. The mixture was stirred for 4 hours. Then, an aqueous sodium thiosulfate solution was added to quench the reaction. The mixture was extracted with diethyl ether three times. The extract was washed with a saturated aqueous sodium chloride solution followed by dehydration over anhydrous sodium sulfate. After the dehydration, the extract was filtered. After distilling the solvent away under a reduced pressure, the filtrate was purified by means of column chromatography (Hexane:Ethyl acetate (AcOEt)=5:1) to give GA07.

Synthetic Example 6

Synthesis of (R)-3,3'-dibromo-1,1'-binaphthol (GA08)

GA07 (5.77 mmol) obtained in Synthetic example 5 and dichloromethane (55 mL) were put in a three-necked round bottom flask and cooled to 0° C. To the solution, A solution prepared by dissolving 7.9 g of Boron tribromide (BBr$_3$, 5.47 mmol) in 20 mL of dichloromethane was added dropwise. After the adding dropwise, the mixture was warmed to room temperature and stirred for additional 5 hours. Then, it was cooled to 0° C., and the reaction was quenched by the addition of water. The solution was extracted with dichloromethane three times. The combined extracts was washed with brine and dried over anhydrous sodium sulfate. After the drying, the extract was filtered. The filtrate was concentrated to give solid material, and the obtained solid was separated and purified by means of column chromatography to give GA08 (5.39 mmol, yield: 93%).

Rf=0.2 (Hexane:$CH_2Cl_2$=2:1).

$^1$H-NMR (400 MHz,$CDCl_3$) δ=8.24 (s,2H), 7.80 (d,2H, J=8.1 Hz), 7.37 (dd,2H,J=8.2,8.1 Hz), 7.29 (dd,2H,J=8.2,8.4 Hz), 7.09 (d,2H,J=8.4 Hz), 5.54 (s,2H).

$^{13}$C-NMR (100 MHz,$CDCl_3$) δ=148.01, 132.75, 129.72, 127.56, 127.38, 124.84, 124.62, 114.62, 112.25.

Synthetic Example 7

Synthesis of (R)-3,3'-dibromo-2,2'-bis(triphenyl siloxy)-1,1'-binaphthyl (GA09)

GA08 (1.89 mmol) obtained in Synthetic example 6 and DMF were put in a two-necked round bottom flask. To the flask, Imidazole (5.29 mmol) and Triphenylsilyl chloride (5.79 mmol) were added, and the reaction mixture was stirred at room temperature for 5 hours. After 5 hours, disappearance of GA08 was checked by means of TLC. Then, the solution was cooled to 0° C., and the reaction was quenched by the addition of a saturated aqueous sodium hydrogen carbonate solution dropwise. The reaction mixture was extracted with ethyl acetate three times. The combined extracts was washed with 1 M hydrochloric acid and brine, and dried over anhydrous sodium sulfate. After the drying, the extract was filtered, and the filtrate was concentrated. The obtained solid was separated and purified by means of column chromatography to give GA09 (1.87 mmol, yield: 99%).

Rf=0.4 (Hexane:$CH_2Cl_2$=2:1).

$^1$H-NMR (400 MHz,$CDCl_3$) δ=7.65 (s,2H), 7.46 (d,2H, J=7.5 Hz), 7.41-7.35 (m,4H), 7.28-7.24 (m,20H), 7.18-7.02 (m,20H), 6.82 (d,2H,J=8.6 Hz).

Synthetic Example 8

Synthesis of (R)-3,3'-bis(triphenylsilyl)-1,1'-binaphthol (GA10)

GA09 (2.69 mmol) obtained in Synthetic example 7 and tetrahydrofuran (40 mL) were put in a three-necked round bottom flask and cooled to 0° C. To the solution, t-Butyllithium (t-BuLi; 5.47 mmol) was added dropwise over 10 minutes or more. After the adding dropwise, the reaction mixture was warmed to room temperature and stirred for additional 1.5 hours. Then, the mixture was cooled to 0° C., a saturated aqueous ammonium chloride solution was added to quench the reaction. The reaction mixture was extracted with dichloromethane three times. The combined extracts was washed with brine and dried over anhydrous sodium sulfate. After the drying, the extract was filtered, and the filtrate was concentrated. The obtained solid was separated and purified by means of column chromatography to give GA10 (2.69 mmol, quant.).

Rf=0.4 (Hexane:$CH_2Cl_2$=2:1).

$^1$H-NMR (400 MHz,$CDCl_3$) δ=7.91 (s,2H), 7.72-7.23 (m,38H), 5.29 (s,2H).

$^{13}$C-NMR (100 MHz,$CDCl_3$) δ=156.51, 142.08, 136.40, 136.31, 135.19, 134.77, 134.28, 129.78, 129.51, 129.23, 129.07, 128.18, 127.82, 127.70, 123.91, 123.85, 123.68, 110.66, 96.14.

Synthetic Example 9

Synthesis of (R)-3,3'-bis(triphenylsilyl)-1,1'-binaphthyl-2,2'-diyl hydrogen-phosphate (GA11)

GA10 (0.94 mmol) obtained in Synthetic example 8 and tetrahydrofuran (8 mL) were put in a two-necked round bottom flask and cooled to −20° C. To the flask, n-BuLi (2.0 mmol) was added dropwise over 5 minutes. The reaction mixture was warmed to room temperature and stirred for additional 2 hours. To the reaction mixture, a solution prepared by diluting phosphoryl chloride (1.1 mmol) in tetrahydrofuran (3.5 mL) was added dropwise over 15 minutes and the mixture was stirred at room temperature for additional 1 hour. Then, distillated water (0.4 mL) and triethylamine were added, and the mixture was heated and refluxed for 5 hours. The reaction mixture was cooled to room temperature. The solvent was distilled away under a reduced pressure. Then the 6 M hydrochloric acid (12 mL) was added. The mixture was heated and refluxed for 5 hours. The reaction mixture was cooled to 0° C. and filtered. The filtrate was washed with water and dried. The obtained solid was separated from the starting materials with Hexane:Toluene=1:1 by means of column chromatography. Then the solid was eluted with toluene to give GA11 (0.54 mmol, yield: 57%).

$^1$H-NMR (400 MHz,$CDCl_3$) δ=8.15 (d,2H,J=9.0 Hz), 7.82 (d,2H,J=8.2 Hz), 7.66-7.60 (m,12H), 7.47-7.14 (m,24H).

Synthetic Example 10

Synthesis of (R)-3,3'-dimesityl-2,2'-dimethoxy-1,1'-binaphthyl (GA13)

GA12 (7.1 mmol) obtained in Synthetic example 2, Ni(ACAC)$_2$ (0.73 mmol) and benzene (40 mL) were put in a three-necked round bottom flask. Mesityl MgBr prepared separately was added dropwise to the solution over 10 minutes or more at room temperature and the reaction mixture was stirred for additional 30 minutes. After that, the mixture was heated and refluxed for 12 hours. The reaction mixture was cooled to 0° C., and the reaction was quenched by the addition of 1 M hydrochloric acid and stirring for 1 hour. The reaction mixture was extracted with diethyl ether three times. The combined extracts was washed with brine and dried over anhydrous sodium sulfate. After the drying, the extract was filtered. The filtrate was concentrated, and separated and purified by means of column chromatography to give GA13 (5.03 mmol, yield: 71%).

Rf=0.3 (Hexane:$CH_2Cl_2$=6:1).

$^1$H-NMR (400 MHz,$CDCl_3$) δ=7.85 (d,2H,J=8.1 Hz), 7.69 (s,2H), 7.41-7.37 (m,2H), 7.26 (s,4H), 6.97 (s,4H), 3.10 (s,6H), 2.35 (s,6H), 2.18 (s,6H), 2.13 (s,6H).

Synthetic Example 11

Synthesis of (R)-3,3'-dimesityl-1,1'-binaphthol (GA14)

GA13 obtained in Synthetic example 10 was subjected to the same deprotection procedure as that in Synthetic example 6 to give GA14 (yield: 95%)

Rf=0.3(Hexane:$CH_2Cl_2$=2:1).

$^1$H-NMR (400 MHz,$CDCl_3$) δ=7.84 (d,2H,J=8.1 Hz), 7.72 (s,2H), 7.36-7.23 (m,6H), 6.98 (s,4H), 5.00 (s,4H), 2.31 (s,6H), 2.13 (s,6H), 2.06 (s,6H).

$^{13}$C-NMR (100 MHz,$CDCl_3$) δ=149.97, 137.71, 137.10, 137.04, 133.39, 132.88, 130.62, 129.43, 129.40, 128.49, 128.41, 128.21, 126.78, 124.51, 123.82, 112.94, 21.11, 20.50, 20.41.

Synthetic Example 12

Synthesis of (R)-3,3'-dimesityl-1,1'-binaphthyl-2,2'-diyl hydrogenphosphate (GA15)

GA14 (1.91 mmol) obtained in Synthetic example 11 and pyridine (7.8 mL) were put in a two-necked round bottom flask. To the flask, phosphoryl chloride (2.69 mmol) was added dropwise over 7 minutes at room temperature and the reaction mixture was stirred for additional 2 hours. After that, the mixture was heated and refluxed for 1 hour. The reaction mixture was cooled to room temperature. Distillated water (1.6 mL) was added dropwise and the mixture was heated and refluxed for 1.5 hours. After that, the mixture was cooled to room temperature, pyridine was distilled away under a reduce pressure. Then 6 M hydrochloric acid (15 mL) was added dropwise, and the mixture was heated and refluxed for additional 2 hours. The reaction mixture was cooled to 0° C. and filtered. The filtrate was washed with water and dried. The extract was recrystallized in methanol to give GA15 (1.30 mmol, yield: 68%).

$^1$H-NMR (400 MHz,CDCl$_3$) δ=7.89 (d,2H,J=8.1 Hz), 7.73 (s,2H), 7.48-7.44 (t,2H,J=7.3 Hz), 7.36 (d,2H,J=8.6 Hz), 7.29 (d,2H,J=7.5 Hz), 6.76 (s,2H), 6.68 (s,2H), 2.13 (s,6H), 2.00 (s,6H), 1.96 (s,6H).

Synthetic Example 13

Synthesis of (R)-3,3'-bis(dihydroxyborane)-2,2'-dimethoxy-1,1'-binaphthyl (GA16)

Diethyl ether (300 mL) and TMEDA (55.1 mmol) were put in a three-necked round bottom flask, to which was added dropwise n-BuLi (56.2 mmol) over 5 minutes or more at room temperature. Further GA06 (19.1 mmol) obtained in Synthetic example 1 was added thereto and the mixture was stirred for 3 hours. The reaction mixture was cooled to −78° C. (EtO)$_3$B (117.5 mmol) was added dropwise over 10 minutes or more. The reaction mixture was warmed to room temperature and stirred overnight. The reaction mixture was cooled to 0° C., the reaction was quenched by the addition of 1 M hydrochloric acid and stirring for 2 hours. The reaction mixture was extracted with diethyl ether three times. The combined extracts was washed with 1 M hydrochloric acid twice and with brine once, and dried over anhydrous sodium sulfate. After the drying, the extract was filtered. The filtrate was concentrated to give a solid, which was recrystallized twice in toluene to give GA16 (12.0 mmol, yield: 63%).

$^1$H-NMR(400 MHz,CDCl$_3$) δ=8.62(s,2H), 7.99(d,2H, J=8.1 Hz), 7.44(t,2H,J=7.6 Hz), 7.32(t,2H,J=7.6 Hz), 7.16(d, 2H,J=8.2 Hz), 6.12(brs,4H), 3.31(s,6H).

Synthetic Example 14

Synthesis of (R)-3,3'-Bis(4-biphenyl)-1,1'-binaphthol (GA18)

GA16 (4.98 mmol) obtained in Synthetic example 13, barium hydroxide octahydrate (14.9 mmol), Pd(PPh$_3$)$_4$ (0.24 mmol), degassed dioxane (33 mL), and distilled water (11 mL) were put in a three-necked round bottom flask and stirred. To the solution, 4-bromobiphenyl (15.0 mmol) was added, and the reaction mixture was heated and refluxed for 22 hours. The reaction mixture was cooled to room temperature, form which dioxane was distilled away under a reduced pressure. 1M hydrochloric acid was added, and then the mixture extracted with dichloromethane three times. The combined extracts was washed with 1M hydrochloric acid twice and with brine once, and dried over anhydrous sodium sulfate. After the drying, the extract was filtered. The filtrate was concentrated to give a solid, and the obtained solid was deprotected in the same procedure as that in Synthetic example 6. 4-Bromobiphenyl was firstly separated from the obtained solid with Hexane:CH$_2$Cl$_2$=4:1 by means of column chromatography, and then GA18 (4.30 mmol, yield: 86%) was separated and purified with Hexane:CH$_2$Cl$_2$=1:1.

Rf=0.5.

$^1$H-NMR (400 MHz,CDCl$_3$) δ=8.08 (s,2H), 7.93 (d,2H, J=7.9 Hz), 7.84-7.81(m,4H), 7.72-7.70 (m,4H), 7.67-7.65 (m,4H), 7.47-7.22 (m,4H), 5.40 (s,2H).

$^{13}$C-NMR (100 MHz,CDCl$_3$) δ=150.23, 140.74, 140.58, 136.41, 132.92, 131.39, 130.24, 130.00, 129.50, 128.80, 128.48, 127.42, 127.40, 127.18, 127.12, 124.40, 124.25, 112.30.

Synthetic Example 15

Synthesis of (R)-3,3'-bis(4-biphenyl)-1,1'-binaphthyl-2,2'-diyl hydrogenphosphate (GA19)

GA18 obtained in Synthetic example 14 was subjected to the same procedure as that in Synthetic example 12 to give a solid content. The solid content was recrystallized in n-hexane and dichloromethane to separate and purify GA19 (1.59 mmol, yield: 84%).

$^1$H-NMR (400 MHz,CDCl$_3$) δ=8.20 (brs,2H), 8.07 (s,2H), 7.97 (d,2H,J=8.1 Hz), 7.88 (d,2H,J=8.1 Hz), 7.62-7.29 (m,20H).

$^{13}$C-NMR (100 MHz,CDCl$_3$) δ=141.32, 140.41, 139.67, 136.88, 133.70, 132.23, 131.26, 130.83, 130.45, 128.73, 128.31, 127.28, 126.99, 126.81, 126.52, 126.26, 126.05, 125.48, 123.14.

Synthetic Example 16

Synthesis of (R)-3,3'-bis(2-naphthyl)-1,1'-binaphthol (GA28)

GA16 (4.98 mmol) obtained in Synthetic example 13, barium hydroxide octahydrate (14.9 mmol), Pd(PPh$_3$)$_4$ (0.24 mmol), degassed dioxane (33 mL), and distilled water (11 mL) were put in a three-necked round bottom flask and stirred. To the solution, 2-bromonaphthalene (15.0 mmol) was added, and the reaction mixture was heated and refluxed for 22 hours. The reaction mixture was cooled to room temperature, dioxane was distilled away under a reduced pressure. After addition of 1 M hydrochloric acid, the mixture was extracted with dichloromethane three times. The combined extracts was washed with 1 M hydrochloric acid twice and with brine once, and dried over anhydrous sodium sulfate. After the drying, the extract was filtered. The filtrate was concentrated to give a solid, the obtained solid was deprotected in the same procedure as that in Synthetic example 6. 2-Bromonaphthalene was firstly separated from the obtained solid with Hexane:CH$_2$Cl$_2$=4:1 by means of column chromatography, and then GA28 (3.26 mmol., yield: 82%) was separated and purified with Hexane:CH$_2$Cl$_2$=2:1.

Rf=0.4.

$^1$H-NMR (400 MHz,CDCl$_3$) δ=8.21 (s,2H), 8.13 (s,2H), 7.96-7.86 (m,10H), 7.53-7.47 (m,4H), 7.43-7.28 (m,6H), 5.46 (brs,2H).

$^{13}$C-NMR (100 MHz,CDCl$_3$) δ=150.30, 135.00, 133.45, 133.03, 132.76, 131.69, 130.63, 129.53, 128.50, 128.20, 127.92, 127.67, 127.43, 126.27, 126.23, 124.40, 124.32, 112.48.

Synthetic Example 17

Synthesis of (R)-3,3'-bis(2-naphthyl)-1,1'-binaphthyl-2,2'-diyl hydrogenphosphate (GA29)

GA28 obtained in Synthetic example 16 was subjected to the same procedure as that in Synthetic example 12 to give a solid content. The obtained solid content was recrystallized in ethanol to give GA29 (1.75 mmol, yield: 72%).

$^1$H-NMR (400 MHz,CDCl$_3$) δ=8.03 (s,4H), 7.97 (d,2H, J=8.4 Hz), 7.69 (d,2H,J=8.1 Hz), 7.59 (d,2H,J=7.3 Hz), 7.47 (d,8H,J=8.1 Hz), 7.33-7.19 (m,6H), 6.53 (brs,1H).

$^{13}$C-NMR (100 MHz,CDCl$_3$) δ=146.09, 142.52, 141.30, 140.53, 135.51, 134.26, 133.01, 132.40, 132.25, 131.31, 131.04, 128.77, 128.39, 128.29, 127.35, 127.14, 126.19, 125.56, 125.39, 124.91, 123.27.

Synthetic Example 18

Synthesis of p-bromo-iodobenzene (GA31)

p-Dibromobenzene and diethyl ether (135 mL) were put in a three-necked round bottom flask and cooled to −78° C., t-BuLi (89.60 mmol) was added dropwise and the reaction mixture was stirred for 30 minutes. To the reaction mixture, iodine (44.90 mmol) dissolved in tetrahydrofuran (15 mL) was added over 15 minutes. The mixture was stirred for 30 minutes, warmed to room temperature, and then stirred for additional 4 hours. The reaction mixture was cooled to 0° C. The reaction was quenched by the addition of a saturated aqueous sodium thiosulfate solution. The reaction mixture was extracted with ethyl acetate three times. The combined extracts was washed with brine and dried over anhydrous sodium sulfate. After the drying, the extract was filtered. The filtrate was concentrated to give a solid, which was recrystallized in ethanol to give GA31 (36.70 mmol, yield: 82%).

$^1$H-NMR (400 MHz,CDCl$_3$) δ=7.56-7.53 (m,2H), 7.26-7.21 (m,2H).

Synthetic Example 19

Synthesis of 2,4,6-trimethylboronic acid (GA33)

Magnesium (60.27 mmol) and tetrahydrofuran (30 mL) were put in a three-necked round bottom flask and stirred. To the solution, bromomesitylene (13.07 mmol) was added, and the reaction mixture was heated. After that, bromomesitylene (32.02 mmol) dissolved in tetrahydrofuran (30 mL) was added dropwise to the solution. The reaction mixture was heated and refluxed for 4.5 hours. Then, the mixture was cooled to −78° C. (EtO)$_3$B (111.66 mmol) was added dropwise over 15 minutes. After that, the mixture was warmed to room temperature and stirred for additional 5 hours. Then the mixture was cooled to 0° C. The reaction was quenched by the addition of 1 M hydrochloric acid and stirring for additional 2 hours. The reaction mixture was extracted with diethyl ether three times. The combined extracts was washed with brine and dried over anhydrous sodium sulfate. After the drying, the extract was filtered. The filtrate was concentrated to give a solid, which was recrystallized in benzene to give GA33 (26.10 mmol, yield: 58%).

$^1$H-NMR (400 MHz,CDCl$_3$) δ=6.82 (s,2H), 4.73 (brs,2H), 2.33 (s,6H), 2.26 (s,3H).
$^{13}$C-NMR (100 MHz,CDCl$_3$) δ=139.64, 138.66, 127.99, 127.26, 22.89, 22.03, 21.12.

Synthetic Example 20

Synthesis of 4-Bromo-2',4',6'-trimethylbiphenyl (GA35)

GA33 (4.98 mmol) obtained in Synthetic example 19, barium hydroxide octahydrate (14.9 mmol), Pd(PPh$_3$)$_4$ (0.24 mmol), degassed dioxane (33 mL), and distillated water (11 mL) were put in a three-necked round bottom flask and stirred. To the solution, GA31 (15.0 mmol) obtained in Synthetic example 18 was added, and the reaction mixture was heated and refluxed for 22 hours. The reaction mixture was cooled to room temperature. Dioxane was distilled away under a reduced pressure. After addition of 1 M hydrochloric acid, the mixture was extracted with dichloromethane three times. The combined extracts was washed with 1 M hydrochloric acid twice and with brine once, and dried over anhydrous sodium sulfate. After the drying, the extract was filtered. By means of column chromatography, the obtained solid was firstly separated with Hexane:CH$_2$Cl$_2$=2:1, and then separated and purified with Hexane:CH$_2$Cl$_2$=1:1 to give GA35 (11.50 mmol, yield: 86%).

Rf=0.6.
$^1$H-NMR (400 MHz,CDCl$_3$) δ=7.52 (d,2H,J=8.2 Hz), 7.00 (d,2H,J=8.2 Hz), 6.92 (s,2H), 2.31 (s,3H), 1.98 (s,6H).
$^{13}$C-NMR (100 MHz,CDCl$_3$) δ=139.95, 137.66, 136.89, 135.74, 131.56, 131.07, 128.13, 120.60, 20.99, 20.68.

Synthetic Example 21

Synthesis of (R)-3,3'-bis[4-(2',4',6'-trimethylbiphenyl)]-1,1'-binaphthol (GA37)

GA16 (4.98 mmol) obtained in Synthetic example 13, barium hydroxide octahydrate (14.9 mmol), Pd(PPh$_3$)$_4$ (0.24 mmol), degassed dioxane (33 mL), and distillated water (11 mL) were put in a three-necked round bottom flask and stirred. To the solution, GA35 (15.0 mmol) obtained in Synthetic example 20 was added, and the reaction mixture was heated and refluxed for 22 hours. The reaction mixture was cooled to room temperature. Dioxane was distilled away under a reduced pressure. After the addition of 1 M hydrochloric acid, the mixture was extracted with dichloromethane three times. The combined extracts was washed with 1 M hydrochloric acid twice and with brine once, and dried over anhydrous sodium sulfate. After the drying, the extract was filtered. The filtrate was concentrated to give a solid, which was deprotected in the same procedure as that in Synthetic example 6. The obtained solid was separated and purified by means of column chromatography to give GA37 (2.85 mmol, yield: 78%).

Rf=0.5 (Hexane).
$^1$H-NMR (400 MHz,CDCl$_3$) δ=8.12 (s,2H), 7.95 (d,2H, J=8.2 Hz), 7.81 (d,2H,J=8.4 Hz), 7.42-7.39 (m,2H), 7.36-7.32 (m,2H), 7.28-7.24 (m,6H), 6.97 (s,4H), 5.45 (s,2H), 2.34 (s,6H), 2.07 (s,12H).
$^{13}$C-NMR (100 MHz,CDCl$_3$) δ=150.18, 140.59, 138.61, 136.67, 136.03, 135.56, 132.95, 131.37, 130.46, 129.54, 129.47, 128.44, 128.10, 127.32, 124.34, 124.31, 112.47, 21.02, 20.86.

Synthetic Example 22

Method of synthesizing (R)-3,3'-bis[4-(2',4',6'-trimethylbiphenyl)]-1,1'-binaphthyl-2,2'-diyl hydrogenphosphate (GA38)

GA37 (1.91 mmol) obtained in Synthetic example 21 and pyridine (7.8 mL) were put in a two-necked round bottom flask, phosphoryl chloride (2.69 mmol) was added dropwise over 7 minutes at room temperature, and the reaction mixture was stirred for additional 2 hours. After that, the mixture was heated and refluxed for 1 hour. The reaction mixture was cooled to room temperature. Distillated water (1.6 mL) was added dropwise and the mixture was heated and refluxed for 1.5 hours. After that, the mixture was cooled to room temperature. Pyridine was distilled away under a reduced pressure. 6 M hydrochloric acid (15 mL) was added dropwise, and the mixture was further heated and refluxed for additional 2 hours. The reaction mixture was cooled to 0° C. and filtered. The filtrate was washed with water and dried. The extract was recrystallized in ethanol to give GA38 (1.75 mmol, yield: 87%).

$^1$H-NMR (400 MHz,CDCl$_3$) δ=8.35 (brs,1H), 8.07 (s,2H), 7.92 (d,2H,J=8.1 Hz), 7.51-7.43 (m,4H), 7.33-7.24 (m,4H), 7.17 (d,4H,J=8.1 Hz), 2.32 (s,6H), 1.98 (s,12H).
$^{13}$C-NMR (100 MHz,CDCl$_3$) δ=142.15, 139.97, 138.73, 136.31, 135.95, 135.72, 134.11, 132.19, 131.19, 130.95, 130.06, 128.95, 128.22, 127.90, 127.03, 126.08, 125.88, 125.35, 123.07, 20.97, 20.71.

Synthetic Example 23

Method of synthesizing 2-naphthylboronic acid (GA40)

Magnesium (60.27 mmol) and tetrahydrofuran (30 mL) were put in a three-necked round bottom flask and stirred. To the solution, 2-bromonaphthalene (13.07 mmol) was added, and the reaction mixture was heated. After that, 2-bromonaphthalene (32.02 mmol) dissolved in tetrahydrofuran (30 mL) was added dropwise to the solution. The reaction mixture was heated and refluxed for 4.5 hours. After that, the mixture was cooled to −78° C. (EtO)$_3$B (111.66 mmol) was added dropwise over 15 minutes. Then, the mixture was warmed to room temperature and stirred for additional 5 hours. Then, the mixture was cooled to 0° C. The reaction was quenched by the addition of 1 M hydrochloric acid stirring for 2 hours. The reaction mixture was extracted with diethyl ether three times. The combined extracts was washed with brine and dried over anhydrous sodium sulfate. After the drying, the extract was filtered. Then the filtrate was concentrated. The obtained solid was recrystallized in benzene to give GA40 (9 mmol, yield: 77%).

$^1$H-NMR (400 MHz,CDCl$_3$) δ=8.91 (s,1H), 8.35 (d,1H, J=8.2 Hz), 8.11 (d,1H,J=7.3 Hz), 8.01 (d,1H,J=8.2 Hz), 7.96 (d,1H,J=7.3 Hz), 7.64 (m,2H).
$^{13}$C-NMR (100 MHz,CDCl$_3$) δ=137.89, 135.88, 132.91, 130.68, 129.12, 127.89, 127.67, 127.37, 126.05.

Synthetic Example 24

Method of synthesizing 2-(4-Bromonaphthyl)naphthalene (GA42)

GA40 (4.98 mmol) obtained in Synthetic example 23, barium hydroxide octahydrate (14.9 mmol), Pd(PPh$_3$)$_4$ (0.24 mmol), degassed dioxane (33 mL), and distilled water (11 mL) were put in a three-necked round bottom flask and stirred. To the solution, GA31 (15.0 mmol) obtained in Synthetic example 18 was added, and the reaction mixture was heated and refluxed for 22 hours. The reaction mixture was cooled to room temperature. Dioxane was distilled away under a reduced pressure. After the addition of 1 M hydrochloric acid, the mixture was extracted with dichloromethane three times. The combined extracts were washed with 1 M hydrochloric acid twice and with brine once, and dried over anhydrous sodium sulfate. After the drying, the extract was filtered. The filtrate was concentrated to give a solid, which was deprotected in the same procedure as that in Synthetic example 6. The obtained solid was separated and purified by means of column chromatography to give GA42 (7.02 mmol, yield: 79%).
Rf=0.6 (Hexane).
$^1$H-NMR (400 MHz,CDCl$_3$) δ=8.01 (s,1H), 7.93-7.85 (m,3H), 7.77-7.68 (m,1H), 7.60-7.59 (m,4H), 7.57-7.48 (m,2H).
$^{13}$C-NMR (100 MHz,CDCl3) δ=140.03, 137.29, 133.59, 132.71, 131.95, 128.97, 128.62, 128.18, 127.66, 126.47, 126.17, 125.72, 125.13, 121.64, 106.35.

Synthetic Example 25

Synthesis of (R)-3,3'-bis(4-naphthalen-2-yl-phenyl)-1,1'-binaphthol (GA44)

GA16 (4.98 mmol) obtained in Synthetic example 13, barium hydroxide octahydrate (14.9 mmol), Pd(PPh$_3$)$_4$ (0.24 mmol), degassed dioxane (33 mL), and distilled water (11 mL) were put in a three-necked round bottom flask and stirred. To the solution, GA42 (15.0 mmol) obtained in Synthetic example 24 was added, and the reaction mixture was heated and refluxed for 22 hours. The reaction mixture was cooled to room temperature. Dioxane was distilled away under a reduced pressure. After the addition of 1 M hydrochloric acid, the mixture was extracted with dichloromethane three times. The combined extracts was washed with 1 M hydrochloric acid twice and with brine once, and dried over anhydrous sodium sulfate. After the drying, the extract was filtered, and the filtrate was concentrated. A obtained solid was separated and purified by means of silica gel column chromatography (Hexane:CH$_2$Cl$_2$=2:1 to Hexane: CH$_2$Cl$_2$=1:1). However, since GA42 could not completely be removed, it was separated and purified again by means of neutral alumina column chromatography (benzene to ethyl acetate) to give GA44 (1.61 mmol, yield: 57%).
Rf=0.5.
$^1$H-NMR (400 MHz,CDCl$_3$) δ=8.11 (s,4H), 7.96-7.23 (m,18H), 7.52-7.23 (m,10H), 5.44 (s,2H).
$^{13}$C-NMR (100 MHz,CDCl$_3$) δ=150.28, 140.44, 138.02, 136.52, 133.68, 132.96, 132.69, 131.42, 130.25, 130.12, 129.53, 128.49, 128.22, 127.65, 127.46, 127.42, 126.32, 125.99, 125.80, 125.47, 124.43, 124.27, 112.31.

Synthetic Example 26

Synthesis of (R)-3,3'-bis(4-naphthalen-2-yl-phenyl)-1,1'-binaphthyl-2,2'-diyl hydrogenphosphate (GA45)

GA44 (1.91 mmol) obtained in Synthetic example 25 and pyridine (7.8 mL) were put in a two-necked round bottom flask. To the solution, phosphoryl chloride (2.69 mmol) was added dropwise over 7 minutes at room temperature, and the reaction mixture was stirred for additional 2 hours. After that, the mixture was heated and refluxed for 1 hour. The reaction mixture was cooled to room temperature. Distilled water (1.6 mL) was added dropwise, and the mixture heated and refluxed for 1.5 hours. After that, the mixture was cooled to room temperature. Pyridine was distilled away under a reduced pressure. 6 M hydrochloric acid (15 mL) was added dropwise, and then the mixture was heated and refluxed for additional 2 hours. The reaction mixture was cooled to 0° C. and filtered. The filtrate was washed with water and dried. The solid was recrystallized in Toluene/Hexane to give GA45 (1.15 mmol, yield: 79%).
$^1$H-NMR (400 MHz,CDCl$_3$) δ=8.06 (s,2H), 7.95 (d,4H, J=7.5 Hz), 7.90 (d,4H,J=8.1 Hz), 7.85-7.81 (m,6H), 7.68-7.64 (m,6H), 7.48-7.45 (m,6H), 7.40 (d,2H,J=8.8 Hz), 7.28 (m,12H), 7.15 (brs,1H).
$^{13}$C-NMR (100 MHz,CDCl$_3$) δ=146.10, 141.45, 139.12, 137.61, 136.98, 133.94, 133.50, 132.45, 132.29, 131.19, 130.73, 130.59, 128.31, 128.17, 127.50, 127.04, 126.77, 126.12, 125.78, 125.48, 125.34, 125.19, 123.18.

Synthetic Example 27

Synthesis of (R)-2,2'-bis(methoxymethyloxy)-1,1'-binaphthyl (GB06)

NaH (28.95 mmol) was put in a three-necked round bottom flask and washed with anhydrous diethyl ether twice. To the flask, (R)-BINOL (12.62 mmol) and DMF 60 ml were added, and the reaction mixture was stirred at 0° C. for 30 minutes. Subsequently, Methoxymethyl chrolide (MOMCl; 31.89 mmol) was added dropwise at 0° C. over 10 minutes. After being warmed to room temperature, the mixture was stirred for additional 1 hour. The reaction was quenched by the addition of water and 1 M hydrochloric acid and stirring for a few minutes. The mixture was extracted with ethyl acetate three times. The extract was washed with a saturated aqueous sodium chloride solution, and dehydrated over anhydrous sodium sulfate. After the dehydration, the extract was filtered. Then the solvent was distilled away from the filtrate under a reduced pressure to give GB06 (12.59 mmol, quant.).

Synthetic Example 28

Synthesis of (R)-2,2'-bis(methoxymethyloxy)-3,3'-dibromo-1,1'-binaphthyl (GB07)

GB06 (12.6 mmol) obtained in Synthetic example 27 and diethyl ether 200 mL were put in a three-necked round bottom flask. n-BuLi (37.4 mmol) was added at room temperature, and the reaction mixture stirring for 3 hours. The reaction mixture was cooled to 0° C. A solution prepared by dissolving $CF_2Br$—$CF_2Br$ (37.4 mmol) in THF 50 mL was added dropwise. After the adding dropwise, the mixture was warmed to room temperature and stirred for additional 4 hours. After that, the reaction was quenched by the addition of a saturated aqueous sodium chloride solution. The mixture was extracted with diethyl ether three times. The extract was washed with a saturated aqueous sodium chloride solution, and dehydrated over anhydrous sodium sulfate. After the dehydration, the extract was filtered. After distilling the solvent away under a reduced pressure, the filtrate was purified by means of column chromatography (Hexane:AcOEt=5:1) to give GB07 (12.13 mmol, yield: 96%).

Synthetic Example 29

Synthesis of GB08 (Formula (19))

p-Bromoanisole (26.46 mmol) and THF 20 mL were put in a three-necked round bottom flask and cooled to −78° C. n-BuLi (29.83 mmol) was added dropwise thereto over 12 minutes, and the reaction mixture was stirred at −78° C. for additional 1 hour. After that, triethyl borate (29.45 mmol) was added dropwise to the reaction mixture over 9 minutes, and the mixture was stirred at −78° C. for 1.5 hours. After the stirring, the reaction was quenched at −78° C. by the addition of a saturated aqueous ammonium chloride solution. After being warmed to room temperature, 100 ml of water was added, and the mixture was extracted with diethyl ether. The extract was washed with a saturated aqueous sodium hydrogen carbonate solution and a saturated aqueous sodium chloride solution, and dehydrated over anhydrous sodium sulfate. After the dehydration, the extract was filtered. After distilling the solvent away under a reduced pressure, the filtrate was crystallized in water to give GB08 (7.57 mmol, yield: 28%) represented by formula (19).

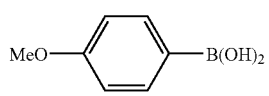

(19)

Synthetic Example 30

Synthesis of (R)-3,3'-bis(p-methoxyphenyl)-1,1'-binaphthol (GB11)

After $Pd(PPh_3)_4$ (0.083 mmol) and DME 6 mL were put in a three-necked round bottom flask, a solution prepared by dissolving GB07 (2.52 mmol) obtained in Synthetic example 28 in DME 8 mL was added. Then, GB08 (7.57 mmol) obtained in Synthetic example 29 and 2.4 mL of a 4 M aqueous sodium carbonate solution were further added, and the reaction mixture was stirred for 18 hours under reflux. Then, the mixture was cooled to room temperature and filtered. From the filtrate, the solvent was distilled away under a reduced pressure. After the concentration, a suitable amount of dichloroethane was added, and the mixture was washed with water and a saturated aqueous sodium chloride solution, and dehydrated over anhydrous sodium sulfate. After the dehydration, the mixture was filtered. Then the solvent in the filtrate was distilled away under a reduced pressure. The dried product, 10 ml of THF, and 0.4 ml of concentrated hydrochloric acid were put in a two-necked round bottom flask and stirred at 50° C. for 2 hours. The mixture was cooled to room temperature. The reaction was quenched at 0° C. by the addition of a saturated aqueous sodium hydrogen carbonate solution. After that, the mixture was extracted with diethyl ether three times. The extract was washed with a saturated aqueous sodium chloride solution, and dehydrated over anhydrous sodium sulfate. After the dehydration, the extract was filtered. After distilling the solvent away under a reduced pressure, the filtrate was purified by means of column chromatography (Hexane:AcOEt=4:1) to give GB11 (1.14 mmol, yield: 45%).

$^1$H-NMR (400 MHz, $CDCl_3$) δ=3.85 (6H,S), 5.35 (2H,S), 7.00 (4H,d), 7.18 (2H,d), 7.27 (2H,dd), 7.35 (2H,dd), 7.64 (4H,d), 7.87 (2H,d), 7.96 (2H,s)

Synthetic Example 31

Synthesis of (R)-3,3'-bis(p-methoxyphenyl)-1,1'-binaphthyl-2,2'-diyl hydrogen-phosphate (GB15)

GB11 (1.02 mmol) obtained in Synthetic example 30 and 1.4 ml of pyridine were put in a two-necked round bottom flask. $POCl_3$ (1.45 mmol) was added dropwise over 3 minutes, and the reaction mixture was stirred for 1.5 hours under refluxing. The reaction mixture was cooled to room temperature, and water (150 µL) was added over 5 minutes. Then, after stirring for 2 hours under refluxing, the mixture was cooled to room temperature. From the reaction mixture, pyridine was distilled away under a reduced pressure. After that, 6 M hydrochloric acid (7 mL) was added over 10 minutes, and the mixture was stirred for 2.5 hours under refluxing. The mixture was cooled to 0° C. and filtered. The filtered residue was washed with water and crystallized in ethanol to give GB15 (0.37 mmol, yield: 37%).

Synthetic Example 32

Synthesis of (R)-3,3'-bis[4-(trifluoromethyl)phenyl]-1,1'-binaphthol (GB14)

GA16 (3.73 mmol) obtained in Synthetic example 13, barium hydroxide octahydrate (11.03 mmol), $Pd(PPh_3)_4$ (0.14 mmol), 1,4-dioxane 24 ml, and 8 mL of water were put in a three-necked round bottom flask and stirred. To the solution, 4-Bromobenzotrifluoride (12.14 mmol) was added dropwise over 10 minutes. The solution was refluxed for 24 hours. After that, 1,4-dioxane was distilled away under a reduced pressure, and then dichloromethane was added. The mixture was washed with 1 M hydrochloric acid and a saturated aqueous sodium chloride solution, and dehydrated over anhydrous sodium sulfate. The above product and 100 mL of dichloromethane were put in a three-necked round bottom flask and then cooled to 0° C. BBr$_3$ (16.76 mmol, a 1 M dichloromethane solution) was added dropwise. After completing the adding dropwise, the mixture was stirred at room temperature for 8.5 hours and then cooled again to 0° C. The reaction was quenched by the addition of 120 ml of water. The mixture was washed with water and a saturated aqueous sodium chloride solution followed by dehydration over anhydrous sodium sulfate. The solvent was distilled away under a reduced pressure. The residue was purified by means of column chromatography (Hexane:AcOEt=5:1) to give GB14 (2.29 mmol, yield: 61%).

Synthetic Example 33

Synthesis of (R)-3,3'-bis[4-(trifluoromethyl)phenyl]-1,1'-binaphthyl-2,2'-diyl hydrogenphosphate (GB16)

GB14 (1.02 mmol) obtained in Synthetic example 32 and 1.4 mL of pyridine were put in a two-necked round bottom flask. POCl$_3$ (1.45 mmol) was added dropwise over 3 minutes, and the reaction mixture was refluxed for 1.5 hours. The reaction mixture was cooled to room temperature. Water (150 μL) was added over 5 minutes. After that, the mixture was refluxed for 2 hours, and cooled to room temperature. Then, pyridine was distilled away from the reaction mixture under a reduced pressure. 6 M hydrochloric acid (7 mL) was added over 10 minutes followed by refluxing for 2.5 hours. The mixture was cooled and purified by means of silica gel column chromatography containing triethylamine, and then made into a free salt form with 6 M hydrochloric acid to give GB16.

Synthetic Example 34

Synthesis of (R)-3,3'-bis(4-nitrophenyl)-1,1'-binaphthol (GC01)

GA16 (4 mmol) obtained in Synthetic example 13, barium hydroxide octahydrate (12 mmol), Pd(PPh$_3$)$_4$ (0.28 mmol), 24 mL of 1,4-dioxane, and 8 mL of water were put in a three-necked round bottom flask and stirred. To the solution, 1-Bromo-4-nitrobenzene (10 mmol) was added dropwise, and the reaction mixture was refluxed for 25 hours. After that, 1,4-dioxane was distilled away under a reduced pressure, and then dichloromethane was added. The mixture was washed with 1 M hydrochloric acid and a saturated aqueous sodium chloride solution, and dehydrated over anhydrous sodium sulfate. The above product and 100 mL of dichloromethane were put in a three-necked round bottom flask, which was cooled to 0° C. BBr$_3$ (18 mmol, a 1 M dichloromethane solution) was added dropwise. After completion of the addition dropwise, the mixture was stirred at room temperature for 8.5 hours and cooled again to 0° C. The reaction was quenched by the addition of 120 mL of water. The mixture was washed with water and a saturated aqueous sodium chloride solution, and dehydrated over anhydrous sodium sulfate. The solvent was distilled away under a reduced pressure. The residue was purified by means of column chromatography (Hexane:AcOEt=5:1) to give GC01 (yield: 82%).

Synthetic Example 35

Synthesis of (R)-3,3'-bis(4-nitrophenyl)-1,1'-binaphthyl-2,2'-diyl hydrogen-phosphate (GC02)

GC01 (1 mmol) and 1.4 mL of pyridine were put in a two-necked round bottom flask. POCl$_3$ (1.4 mmol) was added dropwise over 3 minutes, and the reaction mixture was stirred at room temperature for 2 hours. To the reaction mixture, water (150 μL) was added, and the mixture was stirred for additional 30 minutes. After that, pyridine was distilled away from the reaction mixture under a reduced pressure. After that, 6 M hydrochloric acid (7 mL) was added, and the mixture was refluxed for 2 hours. The mixture was cooled and purified by means of silica gel column chromatography containing triethylamine, which was made into a free salt form with 6 M hydrochloric acid. The free salt form was dissolved in a small amount of dichloromethane, and n-hexane was added to precipitate and give GC02 (yield: 62%).

$^1$H-NMR (400 MHz,CDCl$_3$) δ=8.01 (d,2H,J=8.2 Hz), 7.97 (s,2H), 7.92(d,4H,J=8.1 Hz), 7.60-7.55 (m,6H), 7.46-7.21 (m,4H).

Synthetic Example 36

Synthesis of (R)-3,3'-diphenyl-2,2'-dimethoxy-1,1'-binaphthyl (GC03)

GA16 (4 mmol) obtained in Synthetic example 13, Ni(PPh$_3$)$_2$Cl$_2$ (0.32 mmol) and diethyl ether (40 mL) were put in a three-necked round bottom flask. Phenyl MgBr was added dropwise, which had been prepared independently, at room temperature followed by heating and refluxing for 26.5 hours. The reaction mixture was cooled to 0° C., to which was added 1 M hydrochloric acid followed by stirring to quench the reaction. The reaction mixture was extracted with diethyl ether three times. The combined extracts was washed with brine and dried over anhydrous sodium sulfate. After the drying, the extract was filtered. The concentrated filtrate was separated and purified by means of column chromatography to give GC03 (yield: 89%).

Synthetic Example 37

Synthesis of (R)-3,3'-diphenyl-1,1'-binaphthol (GC04)

GC03 obtained in Synthetic example 36 was subjected to the same deprotection operation as that in Synthetic example 6 to give GC04.

Synthetic Example 38

Synthesis of (R)-6,6'-dibromo-3,3'-diphenyl-1,1'-binaphthol (GC05)

GC04 (1 mmol) obtained in Synthetic example 37 was dissolved in dichloromethane and cooled to −78° C. Bromine (2.1 mmol) was added dropwise, the reaction mixture was stirred for 2.5 hours. The reaction mixture was warmed to room temperature. The reaction was quenched by the addition of an aqueous sodium thiosulfate solution. The solution was extracted with diethyl ether. The extract was washed with a saturated aqueous sodium chloride solution, and dehydrated over anhydrous sodium sulfate. After the dehydration, the extract was filtered. The solvent was distilled away from the filtrate under a reduced pressure to give GC05 (yield: 66%).

Synthetic Example 39

Synthesis of (R)-6,6'-dibromo-3,3'-diphenyl-1,1'-binaphthyl-2,2'-diyl hydrogen-phosphate (GC06)

GC05 (1 mmol) obtained in Synthetic example 38 and 1.4 mL of pyridine were put in a two-necked round bottom flask. $POCl_3$ (1.4 mmol) was added, and the reaction mixture was stirred at room temperature for 2 hours. To the reaction, water and sodium hydrogencarbonate were added, and the mixture was additionally stirred. After that, pyridine was distilled away from the reaction mixture under a reduced pressure. 6 M hydrochloric acid (7 mL) was added, and the mixture was refluxed for 2 hours. The mixture was cooled, purified by means of silica gel column chromatography containing triethylamine, which was made into a free salt form with 6 M hydrochloric acid. The free salt form was dissolved in a small amount of dichloromethane, and n-hexane was added to precipitate and give GC06 (yield: 57%).

Synthetic Example 40

Synthesis of silylenolate MK01 (Formula (20))

Tetrahydrofuran (20 mL) and diisopropylamine (30 mmol) were put in a three-necked round bottom flask (200 mL) and stirred at 0° C. After that, n-BuLi (30 mmol) was added dropwise over 5 minutes, and the reaction mixture was stirred for 30 minutes. The mixture was cooled to −78° C. Hexamethylphosphoramide (HMPA; 5.0 mL) and methyl isobutyrate (30.1 mmol) were added dropwise over 5 minutes. The mixture was stirred for 30 minutes. Trimethylsilyl chloride (TMSCl, 35.4 mmol) was added at −78° C. The mixture was warmed to room temperature and stirred for 1 hour, and then cooled to 0° C. The reaction was quenched by the addition of sodium hydrogencarbonate. The reaction mixture was extracted with diethyl ether three times. The combined extracts was washed with brine and dried over anhydrous sodium sulfate. After the drying, the extract was filtered. After removing the solvent, the filtrate was subjected to reduced-pressure distillation (1600 Pa, 69-71° C.) to give silylenolate MK01 represented by formula (20) below.

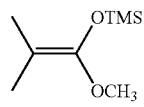

(20)

Synthetic Example 41

Synthesis of silylenolate MK02

The procedure of Synthetic example 40 was repeated except that TMSCl was changed to t-Butyldimethylsilyl chloride (TBSCl) to give MK02.

Synthetic Example 42

Synthesis of silylenolate MK03

The procedure of Synthetic example 40 was repeated except that methyl isobutyrate was changed to isopropyl isobutyrate to give MK03.

Synthetic Example 43

Synthesis of silylenolate MK04

The procedure of Synthetic example 40 was repeated except that methyl isobutyrate was changed to methyl acetate to give MK04.

Synthetic Example 44

Synthesis of imine MI01 (Formula (21))

Imine MI01 represented by formula (21) below was synthesized from Benzaldehyde and 2-Aminophenol.

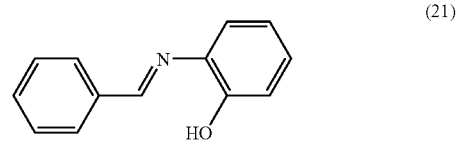

(21)

Synthetic Example 45

Synthesis of (R)-3,3'-Bis[3,5-di(trifluoromethyl)phenyl]-1,1'-binaphthol (GC07)

$Pd(PPh_3)_4$ (0.15 mM, 0.06 eq.), dimethoxyethane (15 mL), 3,5-Bis(trifluoromethyl)bromobenzene (7.54 mM, 3.0 eq.) were put, in this order, in a dried three-necked round bottom flask (100 mL) under nitrogen atmosphere and stirred for 10 minutes. (R)-3,3'-Bis(dihydroxyborane)-2,2'-dimethoxy-1,1'-binaphthyl (2.56 mM) having been diluted with ethanol and 2 N sodium carbonate solution (7.6 mM, 3.0 eq.) were added, and the reaction mixture was heated and refluxed for 18.5 hours. After that, the mixture was cooled to room temperature, and dimethoxyethane was distilled away under a reduced pressure. Then, the residue was dissolved in dichloromethane and 1 N hydrochloric acid, and was extracted with dichloromethane three times. The combined dichloromethane extracts was sequentially washed with 1 N hydrochloric acid and brine, and dried over anhydrous sodium sulfate. After the drying, the extract was filtered. From the product obtained by concentrating the filtrate, a methoxy group was removed. The deprotected product was purified by means of column chromatography to give GC07 (formula (22) below, 1.4 g, 2.01 mM, 79%).

$[\alpha]_D^{26}$: 45.3 (c1.06,$CHCl_3$).

IR ($CHCl_3$): 3522, 1622, 1597, 1502, 1474, 1462, 1427, 1377, 1358, 1335, 1281, 1236, 1182, 1140, 1036, 989, 897, 845 $cm^{-1}$.

Rf=0.3 (Hexane:$CH_2Cl_2$=4:1).

$^1$H-NMR (400 MHz,$CDCl_3$) δ=8.24 (s,4H), 8.12 (s,2H), 8.00 (d,2H,J=7.9 Hz), 7.91 (s,2H), 7.50-7.40 (m,4H), 7.24-7.22 (m,2H), 5.38 (s,2H).

$^{19}$F-NMR (376 MHz,$CDCl_3$) δ=99.01 (s).

$^{13}$C-NMR (100 MHz,$CDCl_3$) δ=149.86, 139.47, 133.24, 132.35, 132.09, 131.76, 131.42, 131.09, 129.85,129.46, 128.90, 128.67, 127.71, 127.49, 125.21, 124.78, 123.97, 122.06, 121.33, 119.35, 111.75.

Anal. Calcd for: C,60.86; H,2.55. Found: C,61.03; H,2.25.

(22)

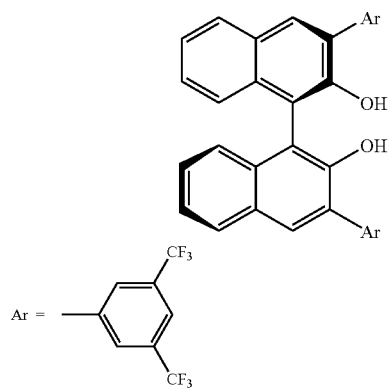

Synthetic Example 46

Synthesis of (R)-3,3'-Bis[3,5-di(trifluoromethyl)phenyl]-1,1'-binaphthyl phosphate (GC08)

Synthesis was conducted in the same procedure as that in the method of obtaining GA15 from GA14. The obtained crude product was recrystallized in dichloromethane/n-hexane, but the recrystallized product included impurities. Thus, it was dissolved in ethanol and reprecipitated with 6 N hydrochloric acid to give (GC08) (formula (23) below, 0.9 g, 1.14 mM, 73%).

$[\alpha]_D^{26}$: −197.5 (c0.97,CHCl$_3$).

IR (CHCl$_3$): 1620, 1501, 1474, 1379, 1325, 1281, 1246, 1178, 1140, 1109, 1084, 1024, 988, 964, 891, 870, 867 cm$^{-1}$.

$^1$H-NMR (400 MHz,CDCl$_3$) δ=8.01 (s,8H), 7.61-7.58 (m,4H), 7.42-7.39 (m,4H).

$^{31}$P-NMR (400 MHz,CDCl$_3$) δ=4.61.

$^{19}$F-NMR (376 MHz,CDCl$_3$) δ=96.63 (s).

$^{13}$C-NMR (100 MHz,CDCl$_3$) δ=143.57, 143.48, 138.55, 132.29, 132.00, 131.94, 131.61, 131.39, 131.27, 131.11, 131.08, 130.94, 129.86, 128.65, 127.56, 127.20, 127.06, 126.77, 124.49, 122.49, 122.47, 121.77, 121.54, 119.06, 96.12.

Anal. Calcd for: C,55.97; H,2.22. Found: C,55.96; H,2.13.

(23)

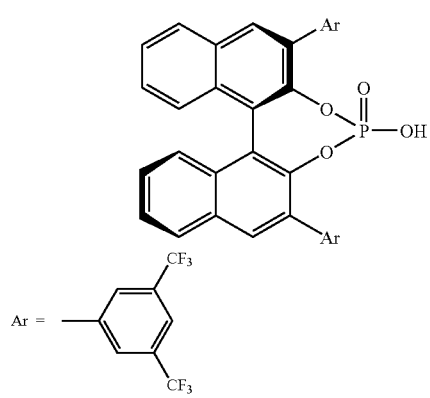

Synthetic Example 47

Synthesis of (R)-3,3'-bis(3,5-dinitrophenyl)-1,1'-binaphthyl phosphate (GC09)

The procedure of Synthetic example 45 was repeated except that 3,5-dinitrobromobenzene was employed to synthesize a compound to which a 3,5-dinitrophenyl group was bonded. Then, the procedure of Synthetic example 46 was repeated to synthesize phosphoric acid ester body GC09 (formula (24)).

(24)

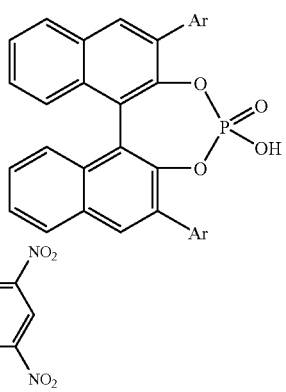

Synthetic Example 48

Synthesis of (R)-3,3'-Bis(2,4,6-triisopropylphenyl)-2,2'-hydroxy-1,1'-dinaphthyl (GC10)

GA07 (5.0 mM), Ni(PPh$_3$)$_2$Cl$_2$ (0.51 mM, 0.1 eq.) and diethyl ether (50 mL) were put, in this order, in a dried three-necked round bottom flask (200 mL) under nitrogen atmosphere and stirred. 2,4,6-Triisopropylphenyl MgBr prepared separately was added dropwise over 7 minutes or more at room temperature. After the adding dropwise, the mixture was stirred for additional 10 minutes, and was heated and refluxed for 24 hours. After that, the mixture was cooled to 0° C. The reaction was quenched by the addition of 1 N hydrochloric acid and stirring. The reaction mixture was extracted with diethyl ether three times. The combined diethyl ether extracts was washed with brine and dried over anhydrous sodium sulfate. After the drying, the extract was filtered. The filtrate was concentrated to give a crude product, which was used in the subsequent step without purification.

The crude product obtained in the previous step and dichloromethane (135 mL) were put, in this order, in a dried three-necked round bottom flask (300 mL) under nitrogen atmosphere and stirred at 0° C. A mixture prepared by diluting boron tribromide (23.28 mM, 4.6 eq.) with dichloromethane (23 mL) was added dropwise over 15 minutes or more. After that, the mixture was warmed to room temperature and stirred for 16 hours. After the stirring, the mixture was cooled to 0° C. The reaction was quenched by the addition of water. The reaction mixture was extracted with dichloromethane three times. The combined dichloromethane extracts was washed with brine and dried over anhydrous sodium sulfate. After the drying, the extract was filtered. The filtrate was concentrated to give a crude product, which was separated and purified by means of column chromatography to give GC10 (2.04 mM, 41%).

$[\alpha]_D^{27}$ 88.8 (c3.03,THF), literature value $[\alpha]_D$ 88.0 (c3.00, THF).

Rf=0.2 (Hexane:CH$_2$Cl$_2$=6:1).

$^1$H NMR (400 MHz,CDCl$_3$) δ=7.87 (d,2H,J=8.2 Hz), 7.77 (s,2H), 7.40-7.12 (m,10H), 4.92 (s,2H), 2.99-2.91 (m,2H), 4.92 (dd,1H,J=2.7,8.4 Hz), 4.44 (d,1H,J=2.7 Hz), 3.89 (s,3H), 3.69 (s,3H), 0.89 (s,9H).

$^{13}$C NMR (100 MHz,CDCl$_3$) δ=150.63, 149.12, 147.80, 147.74, 133.46, 130.63, 130.37, 129.10, 129.04, 128.227, 126.61, 124.52, 123.76, 121.22, 121.15, 113.11, 34.35, 30.89, 30.84, 24.31, 24.29, 24.07, 24.01, 23.92, 23.73.

Anal. Calcd for: C,86.91; H,8.46. Found: C,86.83; H, 8.31.

Synthetic Example 49

Synthesis of (R)-3,3'-bis(2,4,6-triisopropylphenyl)-1, 1'-binaphthyl-2,2'-diyl hydrogenphosphate (GC11)

GC10 was subjected to the same procedure as that in Synthetic example 12. A crude product obtained in the procedure was separated and purified by means of column chromatography to give GC11 (1.38 mM, 95%).

$[\alpha]_D^{26}$ -59.4 (c1.06,CHCl$_3$).

IR (CHCl$_3$) 2964, 2932, 2870, 1626, 1607, 1568, 1491, 1462, 1412, 1383, 1362, 1317, 1246, 1196, 1151, 1055, 959, 858, 847 cm$^{-1}$.

Rf=0.7 (Hexane:CH$_2$Cl$_2$=10:1).

$^1$H NMR (400 MHz,CDCl$_3$) δ=7.88-7.84 (m,2H), 7.80 (s,2H), 7.45-7.41 (m,2H), 7.32-7.25 (m,4H), 7.02 (s,2H), 6.95 (s,2H), 2.94-2.82 (m,4H), 2.71-2.65 (m,2H), 1.23 (d,12H,J=6.8 Hz), 1.13-1.10 (m,12H), 1.03 (d,6H,J=6.8 Hz), 0.92 (d,6H,J=6.8 Hz).

$^{31}$P NMR (400 MHz,CDCl$_3$) δ=4.02.

$^{13}$C NMR (100 MHz,CDCl$_3$) δ=148.06, 147.56, 147.47, 147.33, 142.69, 142.22, 132.92, 132.67, 131.92, 130.50, 128.02, 127.20, 125.76, 125.64, 124.85, 122.48, 120.84, 119.95, 34.14, 30.91, 30.72, 26.33, 24.93, 24.15, 24.02, 23.50, 23.31.

Anal. Calcd for: C,79.76; H,7.63. Found: C,79.52; H,7.87.

Synthetic Example 50

Synthesis of (R)-5,5',6,6',7,7',8,8'-Octahydro-1,1'-bi-2-naphthol (CD01)

(R)-BINOL (70.52 mM), platinum oxide (1.15 mM), and acetic acid (25 mL) were put in an autoclave in this order and stirred under a hydrogen atmosphere of 6.8 atoms at room temperature for 3 days. The reaction was quenched by the addition of water and dichloromethane. The reaction mixture was extracted with dichloromethane three times. The dichloromethane extract was washed with water once and with a saturated aqueous sodium hydrogen carbonate solution twice, and dried over anhydrous sodium sulfate. After the drying, the extract was filtered. The filtrate was concentrated to give CD01 (70.74 mM, quant., formula (25) below).

$[\alpha]_D^{26}$ 47.1 (c 1.04,CHCl$_3$).

$^1$H NMR (400 MHz,CDCl$_3$) δ=7.06 (d,2H,J=8.2 Hz), 6.82 (d,2H,J=8.2 Hz), 4.60 (s,2H), 2.75 (t,4H,J=6.2 Hz), 2.33-2.25 (m,2H), 2.19-2.12 (m,2H), 1.77-1.64 (m,8H).

$^{13}$C NMR (100 MHz,CDCl$_3$) δ=151.35, 137.12, 131.01, 130.08, 118.81, 112.93, 29.20, 27.08, 22.98, 22.92.

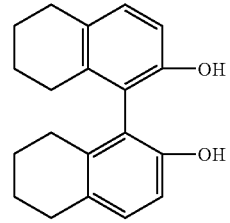

(25)

Synthetic Example 51

Synthesis of (R)-5,5',6,6',7,7',8,8'-Octahydro-1,1'-bi-2-naphthyl phosphate (GD02)

The same procedure as that in the method of synthesizing GC02 was repeated to synthesize GD02 from GD01. After the synthesis, the crude was reprecipitated in methanol and water to give GD02 (formula (26) below, 1.35 mM, yield: 57%).

$[\alpha]_D^{25}$ -239.7 (c1.01,EtOH)

$^1$H NMR (400 MHz,CDC$_3$) δ=7.11 (d,2H,J=8.4 Hz), 7.06 (d,2H,J=8.4 Hz), 4.82 (brs,1H), 2.86-2.63 (m,6H), 2.31-2.24 (m,2H), 1.82-1.77 (m,6H), 1.57-1.52(m,2H).

$^{31}$P NMR (400 MHz,CDCl$_3$) δ=2.04.

$^{13}$C NMR (100 MHz,CDCl$_3$) δ=146.35, 138.27, 135.46, 129.93, 126.08, 118.11, 29.09, 27.79, 22.44, 22.29.

Anal. Calcd for: C,67.41; H,5.94. Found: C,67.62; H,6.01.

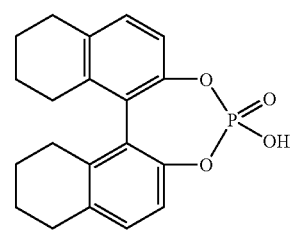

(26)

Synthetic Example 52

Synthesis of (R)-3,3'-Dibromo-5,5',6,6',7,7',8,8'-octahydro-1,1'-bi-2-naphthol (GD03)

GD01 (3.48 mM) and dichloromethane (20 mL) were put, in this order, in a dried three-necked round bottom flask (100 mL) under nitrogen atmosphere and stirred. Subsequently, bromine (8.53 mM) was added dropwise over 16 minutes at room temperature. Then, after stirring the mixture at room temperature for 16.5 hours (disappearance of GD01 was checked by means of TLC), the mixture was cooled to 0° C. The reaction was quenched by the addition of a saturated aqueous sodium sulfite solution. The reaction mixture was extracted with dichloromethane three times. The combined dichloromethane extracts was washed with brine and dried over anhydrous sodium sulfate. After the drying, the extract was filtered. The filtrate was concentrated to give GD03 (3.64 mM, quant.).

$^1$H NMR (400 MHz,CDCl$_3$) δ=7.28 (s,2H), 5.11 (s,2H), 2.74-2.73 (m,4H), 2.32-2.26 (m,2H), 2.12-2.06 (m,2H), 1.76-1.61 (m,8H).

Synthetic Example 53

Synthesis of (R)-3,3'-Dibromo-5,5',6,6',7,7',8,8'-octahydro-2,2'-methoxymethyl-1,1'-binaphthyl (GD04)

Sodium hydride (24.10 mM, having been washed with diethyl ether) and DMF (40 mL) were put, in this order, in a dried three-necked round bottom flask (200 mL) under nitrogen atmosphere and stirred at 0° C. GD03 (9.73 mM) dissolved in DMF (30 mL) was added, and the reaction mixture was stirred for 20 minutes. Subsequently, MOMCl (25.02 mM) was added dropwise over 3 minutes at 0° C. Two hours after warming the mixture to room temperature (disappearance of GD03 was checked by means of TLC), the mixture was cooled to 0° C. The reaction was quenched by the addition of water, ethyl acetate and 1 N hydrochloric acid. The reaction mixture was extracted with ethyl acetate three times. The combined ethyl acetate extracts was washed sequentially with 1 N hydrochloric acid and brine and dried over anhydrous sodium sulfate. After the drying, the extract was filtered. The filtrate was concentrated to give GD04 (9.88 mM, quant.).

$^1$H NMR (400 MHz,CDCl$_3$) δ=7.32 (s,2H), 4.93 (d,2H, J=5.7 Hz), 4.83 (d,2H,J=5.7 Hz), 2.86 (s,6H), 2.76-2.71 (m,4H), 2.44-2.38 (m,2H), 2.14-2.09 (m,2H), 1.75-1.60(m, 8H).

Synthetic Example 54

Synthesis of (R)-3,3'-Diphenyl-5,5',6,6',7,7',8,8'-octahydro-1,1'-binaphthol (GD05)

Barium hydroxide octahydrate (12.02 mM, 3.0 eq.), phenylboric acid (12.01 mM, 3.0 eq.), Pd(PPh$_3$)$_4$ (0.25 mM, 0.06 eq.), GD04 (4.02 mM), dioxane (27 mL), and distilled water (9 mL) were put, in this order, in a dried three-necked round bottom flask (100 mL) under nitrogen atmosphere and heated and refluxed for 3 hours. After that, the mixture was cooled to room temperature, and dioxane was distilled away under a reduced pressure. Then, dichloromethane and 1 N hydrochloric acid were added. The reaction mixture was extracted with dichloromethane three times. The combined dichloromethane extracts was washed with 1 N hydrochloric acid and brine, and dried over anhydrous sodium sulfate. After the drying, the extract was filtered. The filtrate was concentrated to give a solid. Ethanol (50 mL) and concentrated hydrochloric acid (12 mL) were added to the solid, and the reaction mixture was heated and refluxed for 10 hours. After the refluxing, ethanol was distilled away from the reaction mixture under a reduced pressure. The mixture was extracted with dichloromethane three times. The combined dichloromethane extracts was washed with brine and dried over anhydrous sodium sulfate. After the drying, the extract was filtered. The filtrate was concentrated to give a solid, which was separated and purified by means of column chromatography to give GD05 (2.23 mM, 55%).

[α]$_D^{25}$–19.0 (c0.40,CHCl$_3$), literature value [α]$_D^{25}$–29.3 (c0.41,CHCl$_3$).

Rf=0.2 (Hexane:Ethyl acetate=15:1)

$^1$H NMR (400 MHz,CDCl$_3$) δ=7.61-7.58 (m,4H), 7.45-7.40 (m,4H), 7.34-7.29 (m,2H), 7.15 (s,2H), 4.91 (s,2H), 2.82-2.78 (m,4H), 2.44-2.38 (m,2H), 2.30-2.22 (m,2H), 1.76-1.74 (m,8H).

$^{13}$C NMR (100 MHz,CDCl$_3$) δ=147.92, 137.78, 136.44, 131.59, 130.08, 129.09, 128.26, 126.97, 125.92, 120.04, 29.37, 27.28, 23.18, 23.16.

Synthetic Example 55

Synthesis of (R)-5,5',6,6',7,7',8,8'-Octahydro-3,3'-bisphenyl-1,1'-binaphthyl phosphate (GD06)

The same procedure as that in the method of synthesizing GC02M was repeated to synthesize GD06 from GD05. By means of column chromatography, the obtained crude product was separated from the starting material (dichloromethane as the solvent), and then was separated and purified with methanol to give GD06 (formula (27) below, 1.18 mM, 75%).

[α]$_D^{25}$–211.3 (c0.99,CHCl$_3$).

IR (CHCl$_3$) 3009, 2939, 2862, 1603, 1501, 145, 1416, 1275, 1225, 1215, 1196, 1157, 1138, 1020, 955, 908, 858 cm$^{-1}$.

$^1$H NMR (400 MHz,CDCl$_3$) δ=7.40 (d,4H,J=7.2 Hz), 7.13-7.01 (m,8H), 4.74 (brs,1H), 2.89-2.64 (m,6H), 2.37-2.30 (m,2H), 1.79-1.59 (m,2H).

$^{31}$P NMR (400 MHz,CDCl$_3$) δ=0.33.

$^{13}$C NMR (100 MHz,CDCl$_3$) δ=143.41, 143.29, 137.24, 137.05, 134.46, 131.53, 130.79, 129.37, 127.97, 127.20, 126.88, 29.29, 27.92, 22.80, 22.69.

Anal. Calcd for: C,75.58; H,5.75. Found: C,75.39; H,5.62.

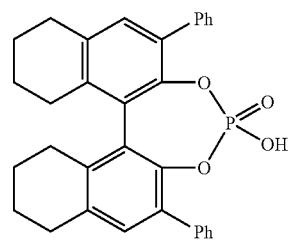

(27)

Synthetic Example 56

Synthesis of (R)-5,5',6,6',7,7',8,8'-Octahydro-2,2'-methoxymethylnaphthol (GD07)

GD01 was subjected to the same procedure as that for GD04 to be methoxymethylated to give GD07 (7.46 mM, quant.) (oil).

$^1$H NMR (400 MHz,CDCl$_3$) δ=7.04 (d,2H,J=8.7 Hz), 6.98 (d,2H,J=8.7 Hz), 5.02 (dd,2H,J=1.3,6.6 Hz), 4.96 (dd,2H, J=1.3,6.6 Hz), 3.29 (s,6H), 2.78-2.75 (m,4H), 2.34-2.26 (m,2H), 2.14-2.08 (m,2H), 1.74-1.64 (m,8H).

$^{13}$C NMR (100 MHz,CDCl$_3$) δ=151.97, 136.61, 130.76, 128.69, 126.93, 112.58, 94.67, 55.64, 29.52, 27.37, 23.30, 23.20.

Synthetic Example 57

Synthesis of (R)-2,2'-Dihydroxy-3,3'-bis(4-nitrophenyl)-5,5',6,6',7,7',8,8'-octahydro-1,1'-dinaphthyl (GD09)

GD07 (2.68 mM) and diethyl ether (50 mL) were put in a dried three-necked round bottom flask (200 mL) under nitrogen atmosphere. n-Butyllithium (10.99 mM) was added dropwise with stirring at room temperature over 8 minutes. After 3 hours, thus prepared mixture was added dropwise to a solution of 2-isopropyloxy-4,4,5,5-tetramethyl-1,3,2-dioxaborolane (12.83 mM) and THF (18 mL), which had been prepared separately, with a cannuler over 24 minutes at −78° C. The mixture was warmed to room temperature, and was stirred for 16 hours. After that, the reaction mixture was filtered over celite, and the filtrate was concentrated. Thus obtained crude product was separated and purified by means of column chromatography to give GD08 (0.6 g, 0.93 mM, 35%).

$[\alpha]_D^{23}$ 58.5 (c1.02,CHCl$_3$).

IR (CHCl$_3$) 2982, 2936, 1595, 1462, 1435, 1389, 1344, 1331, 1308, 1271, 1234, 1211, 1198, 1144, 1034, 991, 928, 856 cm$^{-1}$.

Rf=0.3 (Hexane:Ethyl acetate=5:1)

$^1$H NMR (400 MHz,CDCl$_3$) δ=7.48 (s,2H), 4.95 (dd,2H, J=1.3,6.2 Hz), 4.87 (dd,2H,J=1.3,6.2 Hz), 2.83-2.74 (m,4H), 2.70 (s,6H), 2.53-2.45 (m,2H), 2.18-2.11 (m,2H), 1.72-1.60 (m,8H), 1.32 (s,24H).

$^{13}$C NMR (100 MHz,CDCl$_3$) δ=158.42, 141.46, 136.74, 132.35, 131.32, 100.46, 83.37, 55.76, 29.47, 28.03, 24.89, 24.69, 23.07, 22.98.

Anal. Calcd for: C,68.15; H,8.26. Found: C,68.28; H,8.05.

From GD08, (R)-2,2'-Dihydroxy-3,3'-bis(4-nitrophenyl)-5,5',6,6',7,7',8,8'-octahydro-1,1'-dinaphthyl (GD09, formula (28) below, 1.0 g, 1.91 mM, 97%) was synthesized.

$[\alpha]_D^{25}$ −170.1 (c1.06,CHCl$_3$).

IR (CHCl$_3$) 3520, 3028, 2939, 2862, 1597, 1518, 1462, 1437, 1394, 1346, 1325, 1290, 1234, 1178, 1134, 1109, 856 cm$^{-1}$.

Rf=0.3 (Hexane:Ethyl acetate=8:1)

$^1$H NMR (400 MHz,CDCl$_3$) δ=8.29-8.26 (m,4H), 7.81-7.79 (m,4H), 7.23 (s,2H), 4.92 (s,2H), 2.83-2.82 (m,4H), 2.42-2.36 (m,2H), 2.30-2.24 (m,2H), 1.80-1.76 (m,8H).

$^{13}$C NMR (100 MHz,CDCl$_3$) δ=148.21, 146.44, 144.57, 138.29, 132.03, 131.07, 129.85, 123.89, 123.30, 119.37, 29.28, 27.39, 22.94, 22.92.

Anal. Calcd for: C,71.63; H,5.26; N,5.22. Found: C,71.53; H,5.29; N,5.01.

(28)

Ar = —⌬—NO$_2$

Synthetic Example 58

Synthesis of (R)-3,3'-Bis(4-nitrophenyl)-5,5',6,6',7,7',8,8'-octahydro-1,1'-dinaphthyl phosphate (GD10)

GD09 was subjected to the same procedure as that in the method of synthesizing GC02 to synthesize GD10, from which the raw material was removed by means of column chromatography. The obtained solid was dissolved in methanol, and was purified by the reprecipitation in 6 N hydrochloric acid to give GD10 (formula (29) below, 0.4 g, 0.71 mM, 53%).

$[\alpha]_D^{24}$ −238.5 (c1.00,CHCl$_3$).

IR (CHCl$_3$) 2943, 2843, 1603, 1518, 1435, 1391, 1263, 1217, 1194, 1109, 1022, 955, 899, 854 cm$^{-1}$.

$^1$H NMR (400 MHz,CDCl$_3$) δ=8.09-8.08 (m,4H), 7.64-7.58 (m,4H), 7.21 (s,2H), 2.93-2.88 (m,4H), 2.75-2.72 (m,2H), 2.47-2.43 (m,2H), 1.80-1.82 (m,8H).

$^{31}$P NMR (400 MHz,CDCl$_3$) δ=1.16.

$^{13}$C NMR (100 MHz,CDCl$_3$) δ=146.70, 143.13, 142.21, 142.10, 139.33, 136.20, 130.77, 130.05, 129.27, 126.79, 123.18, 29.34, 28.02, 22.55, 22.40.

Anal. Calcd for: C,64.21; H,4.55; N,4.68. Found: C,64.49; H,4.76; N,4.71.

(29)

Ar = —⌬—NO$_2$

Synthetic Example 59

Synthesis of (R)-3,3'-Bis(4-trifluoromethylphenyl)-2,2'-dihydroxy-5,5',6,6',7,7',8,8'-octahydro-1,1'-dinaphthyl (GD11)

The procedure of GD05 was repeated to give GD11 (0.9 g, 1.60 mM, 80%).

$[\alpha]_D^{25}$ −39.7 (c1.03,CHCl$_3$).

IR (CHCl$_3$) 3522, 2937, 2862, 1618, 1464, 1439, 1396, 1325, 1292, 1236, 1169, 1132, 1111, 1069, 1020, 845 cm$^{-1}$.

$^1$H NMR (400 MHz,CDCl$_3$) δ=7.73 (d,4H,J=8.2 Hz), 7.67 (d,4H,J=8.2 Hz), 7.19 (s,2H), 4.88 (s,2H), 2.83-2.80 (m,4H), 2.43-2.35 (m,2H), 2.29-2.22 (m,2H), 1.79-1.73 (m,8H).

$^{13}$C NMR (100 MHz,CDCl$_3$) δ=148.25, 141.56, 137.57, 132.05, 130.83, 129.52, 129.18, 128.87, 125.66, 125.15, 125.11, 124.81, 122.96, 119.63, 29.21, 27.22, 22.92, 22.90.

$^{19}$F NMR (376 MHz,CDCl$_3$) δ=99.30 (s).

Anal. Calcd for: C,70.10; H,4.84. Found: C,70.36; H,4.89.

Synthetic Example 60

Synthesis of (R)-3,3'-Bis(4-trifluoromethylphenyl)-5,5',6,6',7,7',8,8'-octahydro-1,1'-dinaphthyl phosphate (GD12)

GD11 was subjected to the same procedure as that in method of synthesizing GC02 to synthesize GD12, and then the starting material was separated by means of column chromatography. The obtained solid was dissolved in methanol, and was purified by the reprecipitation in 6 N hydrochloric acid to give GD12 (formula (30) below, 0.5 g, 0.80 mM, 66%).

$[\alpha]_D^{25}$ −171.5 (c1.02,CHCl$_3$).

IR (CHCl$_3$) 2941, 2864, 1620, 1435, 1393, 1325, 1259, 1192, 1167, 1128, 1069, 1022, 957, 901, 845 cm$^{-1}$.

$^1$H NMR (400 MHz,CDCl$_3$) δ=7.54-7.46 (m,8H), 7.13 (s,2H), 2.87-2.86 (m,4H), 2.67-2.64 (m,2H), 2.39-2.34 (m,2H), 1.85-1.80 (m,6H), 1.68-1.60 (m,2H).

$^{31}$P NMR (400 MHz, CDCl$_3$) δ=2.30.

$^{13}$C NMR (100 MHz, CDCl$_3$) δ=142.55, 140.43, 138.55, 135.89, 131.17, 130.26, 129.65, 129.34, 129.03, 126.79, 125.60, 124.98, 124.95, 122.89, 29.19, 27.83, 22.50, 22.34.

$^{19}$F NMR (376 MHz, CDCl$_3$) δ=99.20 (s).

Anal. Calcd for: C,63.36; H,4.22. Found: C,63.61; H,4.09.

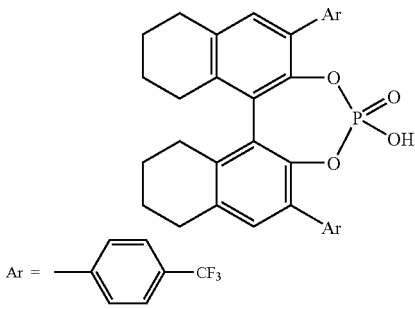

(30)

Example 1

Asymmetric Synthesis by using a Chiral Broensted Acid Catalyst GA04

MI01 (0.15 mmol), GA04 (0.045 mmol) and Ethylbenzene (1 mL) were put in a two-necked round bottom flask and stirred at −80° C. MK01 (0.45 mmol) was added dropwise, and the reaction mixture was stirred at −80° C. for 30.5 hours (Entry 1 in Table 1 below). Entries 2-11 in Table 1 were also subjected to the similar procedure under the conditions shown in Table 1.

After that, the reaction was quenched by the addition of a saturated aqueous sodium hydrogen carbonate solution, and the mixture was warmed to room temperature. The reaction mixture was filtered over celite, and extracted with ethyl acetate three times. The ethyl acetate layer was washed with a saturated aqueous sodium chloride solution, and dehydrated over anhydrous sodium sulfate. After the dehydration, the extract was filtered. The concentrated filtrate was purified by means of preparative TLC (Hexane:AcOEt=3:1) to give Methyl 3-N-(2-hydroxyphenyl)amino-2,2-dimethyl-3-phenylpropionate (P01) represented by formula (31) below.

Here, in the case of Entries 4 and 5 in Table 1, 0.015 mmol of GA04 and 0.09 mmol of GA04 were used, respectively, relative to MI01 (0.15 mmol).

For each P01 obtained in respective Entries, Optical Purity (% ee) was determined by HPLC analysis. These results are shown in Table 1.

Instrumental Analysis Data etc. of P01

Rf=0.4 (Hexane:AcOEt=3:1, developed twice).

$^1$H-NMR (400 MHz, CDCl$_3$) δ=7.29-7.19 (m,5H), 6.69-6.49 (m,3H), 6.39-6.37 (m,1H), 5.80 (brs,1H), 4.93 (brs,1H), 4.57 (s,1H), 3.68 (s,3H), 1.24 (s,3H), 1.21 (s,3H).

$^{13}$C-NMR (100 MHz, CDCl$_3$) δ=177.72, 144.26, 138.97, 135.54, 128.34, 127.92, 127.41, 121.02, 117.92, 114.25, 113.91, 64.58, 52.23, 47.35, 24.36, 20.01.

HPLC: tR=12.6 min., tR=19.8 min.

Daicel Chiralpack AD-H

Hexane/i-Propanol=5/1

UV=244 nm

Flow rate=0.5 ml/min.

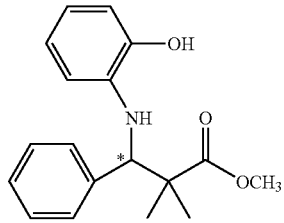

(31)

TABLE 1

| Entry | Solvent | Temperature ° C. | Time hr | Yield % | % ee |
|---|---|---|---|---|---|
| 1 | Ethylbenzene | −80 | 30.5 | quant | 31 |
| 2 | Toluene | −80 | 20 | quant | 27 |
| 3 | Toluene | −80 | 44.5 | 94 | 24 |
| 4 | Toluene | −80 | 46 | 68 | 27 |
| 5 | Toluene | −80 | 26 | quant | 29 |
| 6 | Toluene | 0 | 46.5 | 13 | 15 |
| 7 | o-Xylene | −20 | 46 | 58 | 26 |
| 8 | Mesitylene | −40 | 47 | 86 | 39 |
| 9 | Hexane | −80 | 20 | 20 | 4 |
| 10 | Diethyl ether | −80 | 48 | 34 | 6 |
| 11 | Ethanol | −80 | 17.5 | quant | 2 |

Example 2

Asymmetric Synthesis by using a Chiral Broensted Acid Catalyst GA11

The procedure of Example 1 was repeated except that GA04 was changed to GA11. The result is shown in Table 2.

TABLE 2

| Entry | Solvent | Temperature ° C. | Time hr | Yield % | % ee |
|---|---|---|---|---|---|
| 1 | Mesitylene | −40 | 48 | 4 | 9 |
| 2 | CH$_2$Cl$_2$ | −80 | 37.5 | 19 | 1 |

Example 3

Asymmetric Synthesis by using a Chiral Broensted Acid Catalyst GA15

The procedure of Example 1 was repeated except that GA04 was changed to GA15. The result is shown in Table 3.

TABLE 3

| Entry | Solvent | Temperature ° C. | Time hr | Yield % | % ee |
|---|---|---|---|---|---|
| 1 | THF | −80 | 41 | 51 | 46 |
| 2 | Et$_2$O | −80 | 27 | 30 | 46 |
| 3 | i-Propylbenzene | −80 | 34.5 | 29 | 54 |
| 4 | Ethylbenzene | −80 | 34.5 | 91 | 58 |
| 5 | Toluene | −80 | 26.5 | quant | 60 |
| 6 | Toluene | −80 | 40.5 | 70 | 52 |
| 7 | Mesitylene | −40 | 10 | 95 | 19 |
| 8 | Mesitylene + MS 4A | −40 | 45 | 57 | 62 |
| 9 | CH$_2$Cl$_2$ | −80 | 8.5 | quant | 8 |

Example 4

Asymmetric Synthesis by using a Chiral Broensted Acid Catalyst GA19

The procedure of Example 1 was repeated except that GA04 was changed to GA19. The result is shown in Table 4.

TABLE 4

| Entry | Solvent | Temperature °C. | Time hr | Yield % | % ee |
|---|---|---|---|---|---|
| 1 | $CH_2Cl_2$ | −78 | 3 | quant | 5 |
| 2 | Diethyl ether | −78 | 51 | 21 | 2 |
| 3 | Methanol | −78 | 18.5 | quant | 2 |
| 4 | i-Propylbenzene | −78 | 43 | 40 | 28 |
| 5 | Ethylbenzene | −78 | 39 | 91 | 46 |
| 6 | Toluene | −80 | 40.5 | quant | 56 |
| 7 | m-Xylene | −40 | 46.5 | 40 | 10 |
| 8 | Mesitylene | −40 | 43 | 56 | 15 |

Example 5

Asymmetric Synthesis by using a Chiral Broensted Acid Catalyst GA29

The procedure of Example 1 was repeated except that GA04 was changed to GA29. The result is shown in Table 5.

TABLE 5

| Entry | Solvent | Temperature °C. | Time hr | Yield % | % ee |
|---|---|---|---|---|---|
| 1 | Ethylbenzene | −78 | 43.5 | 69 | 33 |
| 2 | Toluene | −80 | 51 | 83 | 35 |
| 3 | Mesitylene | −40 | 26 | 96 | 29 |
| 4 | Anisole | −35 | 46 | 66 | 12 |

Example 6

Asymmetric Synthesis by using a Chiral Broensted Acid Catalyst GA38

The procedure of Example 1 was repeated except that GA04 was changed to GA38. The result is shown in Table 6.

TABLE 6

| Entry | Solvent | Temperature °C. | Time hr | Yield % | % ee |
|---|---|---|---|---|---|
| 1 | Ethylbenzene | −78 | 47 | 80 | 3 |
| 2 | Toluene | −78 | 59 | 81 | 2 |

Example 7

Asymmetric Synthesis by using a Chiral Broensted Acid Catalyst GA04

MI01 (0.15 mmol), GA04 (0.045 mmol) and Ethylbenzene (1 mL) were put in a two-necked round bottom flask, was cooled to −40° C., and stirred. MK03 (0.474 mmol) was added dropwise, and the reaction mixture was stirred at −40° C. for 17 hours. The mixture was stirred for additional 11 hours at room temperature. Then, the reaction was quenched by the addition of a saturated aqueous sodium hydrogen carbonate solution. The reaction mixture was filtered over celite, and was then extracted with ethyl acetate three times. The ethyl acetate layer was washed with a saturated aqueous sodium chloride solution and dehydrated over anhydrous sodium sulfate. After the dehydration, the extract was filtered. The concentrated filtrate was purified by means of preparative TLC (Hexane:AcOEt=3:1) to give i-Propyl 3-N-(2-hydroxyphenyl)amino-2,2-dimethyl-3-phenylpropionate (P03).

The yield was 8%. The Optical Purity was 33% ee.
Rf=0.3 (Hexane:AcOEt=2:1)
$^1$H-NMR (400 MHz,CDCl$_3$) δ=7.31-7.20 (m,5H), 6.68-6.66 (d,1H,J=7.7 Hz), 6.63-6.59 (t,1H,J=7.7 Hz), 6.54-6.50 (d,1H,J=7.7 Hz), 6.39 -6.37 (m,1H,J=7.7 Hz), 5.19 (brs,1H), 5.06-5.89 (qq,1H,J=7.1,6.2 Hz), 4.91 (brs,1H), 4.53 (s,1H), 1.24-1.22 (d,3H,J=7.1 Hz), 1.22 (s,3H), 1.17 (s,3H), 1.16-1.15 (d,3H,J=6.2 Hz).
HPLC: tR=12.3 min., tR=18.0 min.
Daicel Chiralpack AD-H
Hexane/i-PrOH=9/1
UV=244 nm
Flow rate=0.5 ml/min.

Example 8

Asymmetric Synthesis by using a Chiral Broensted Acid Catalyst GB15

MI01 (0.15 mmol), GB15 (0.045 mmol) and i-Propylbenzene (1 mL) were put in a two-necked round bottom flask and stirred at −78° C. MK01 (0.471 mmol) was added dropwise, and the reaction mixture was stirred at −78° C. for 48 hours (Entry 1 in Table 7 below). Entries 2-4 in Table 7 were also subjected to the similar procedure under the conditions shown in Table 7.

After that, the reaction was quenched by the addition of a saturated aqueous sodium hydrogen carbonate solution, and the mixture was warmed to room temperature. The reaction mixture was filtered over celite, and extracted with ethyl acetate three times. The ethyl acetate layer was washed with a saturated aqueous sodium chloride solution, and dehydrated over anhydrous sodium sulfate. After the dehydration, the extract was filtered. The concentrated filtrate was purified by means of preparative TLC (Hexane:AcOEt=3:1) to give P01.

For each P01 obtained in respective Entries, Optical Purity (% ee) was determined by HPLC analysis. These results are shown in Table 7.

TABLE 7

| Entry | Solvent | Temperature °C. | Time hr | Yield % | % ee |
|---|---|---|---|---|---|
| 1 | i-Propylbenzene | −78 | 48 | 34 | 35 |
| 2 | Toluene | −80 | 48 | 36 | 32 |
| 3 | Mesitylene | −40 | 31 | 54 | 13 |
| 4 | Ethylbenzene | −80 | 48 | 31 | 31 |

Example 9

Asymmetric Synthesis by using a Chiral Broensted Acid Catalyst GC02

MI01 (0.15 mmol), GC02 (0.045 mmol) and Toluene (1 mL) were put in a two-necked round bottom flask and stirred at −78° C. MK01 (0.45 mmol) was added dropwise, and the reaction mixture was stirred at −78° C. for 4 hours (disappearance of MI01 was checked by means of TLC, Entry 1 in Table 8). Entries 2-7 were also subjected to the same procedure under the conditions shown in Table 8.

After that, the reaction was quenched by the addition of a saturated aqueous sodium hydrogen carbonate solution, and the mixture was warmed to room temperature. The reaction mixture was filtered over celite and extracted with ethyl acetate three times. The ethyl acetate layer was washed with 1 M hydrochloric acid and a saturated aqueous sodium chloride solution, and dehydrated over anhydrous sodium sulfate. After the dehydration, the extract was filtered. The concentrated filtrate was purified by means of preparative TLC (Hexane:AcOEt=3:1) to give Methyl 3-N-(2-hydroxyphenyl)amino-2,2-dimethyl-3-phenylpropionate (P01).

For each P01 obtained in respective Entries, Optical Purity (% ee) was determined by HPLC analysis. These results are shown in Table 8.

TABLE 8

| Entry | Solvent | Temperature °C. | Time hr | Yield % | % ee |
|---|---|---|---|---|---|
| 1 | Toluene | −78 | 4 | 96 | 87 |
| 2 | Ethylbenzene | −78 | 4.5 | 100 | 83 |
| 3 | Mesitylene | −78 | 1 | 100 | 77 |
| 4 | Diethylether | −78 | 26 | 98 | 30 |
| 5 | $CH_2Cl_2$ | −78 | 1 | 100 | 13 |
| 6 | Toluene | −40 | 4 | 100 | 81 |
| 7 | Toluene | 0 | 4 | 67 | 73 |

Example 10

Asymmetric Synthesis by using a Chiral Broensted Acid Catalyst GC02

The procedure of Example 9 was repeated except that the ratio of GC02 to MI01 was changed (in this connection, the condition for Entry 1 was the same as that for Entry 1 in Example 9). The results are shown in Table 9.

TABLE 9

| Entry | Solvent | MI01 (mmol) | GC02 (mmol) | Time | Yield | % ee |
|---|---|---|---|---|---|---|
| 1 | Toluene | 0.15 | 0.045 | 4 hr | 96% | 87 |
| 2 | Toluene | 0.15 | 0.015 | 7 hr | 100% | 89 |
| 3 | Toluene | 0.15 | 0.0075 | 20 hr | 100% | 83 |

Example 11

Asymmetric Synthesis by using a Chiral Broensted Acid Catalyst GC06

The procedure of Example 9 was repeated except that GA02 was changed to GA06. The used solvents, reaction temperatures, and results (% ee) are shown in Table 10.

TABLE 10

| Entry | Solvent | Temperature °C. | Time hr | Yield % | % ee |
|---|---|---|---|---|---|
| 1 | Toluene | −78 | 46.5 | 58 | 45 |
| 2 | Ethylbenzene | −78 | 44.5 | 61 | 45 |
| 3 | Mesitylene | −40 | 23 | 99 | 62 |

Example 12

Asymmetric Synthesis by using GC08, GC09 or GB15

MI01 (0.16 mM), GC08 (0.016 mM) as a chiral Broensted acid catalyst, and toluene (1 mL) were put, in this order, in a dried two-necked round bottom flask (10 mL) under nitrogen atmosphere and stirred at −78° C. for 10 minutes. MK01 (0.24 mM) was added dropwise over 3 minutes. After checking disappearance of MI01 by means of TLC, a saturated aqueous sodium hydrogen carbonate solution and a saturated aqueous potassium fluoride solution were added dropwise over 3 minutes, and the mixture was stirred until it was warmed to room temperature to quench the reaction. The reaction mixture was filtered over celite, and extracted with ethyl acetate three times. The combined ethyl acetate extracts was washed sequentially with 1N hydrochloric acid and brine, and dried over anhydrous sodium sulfate. After the drying, the extract was filtered. The concentrated filtrate was separated and purified by means of p-TLC to give a Mannich adduct (P01). Optical purity thereof was determined by means of high-performance mixture chromatography.

GC09 or GB15 was also used for conducting similar asymmetric synthesis. These results are listed in Table 11.

TABLE 11

| Chiral Broensted acid | Reaction time hr | Yield % | % ee |
|---|---|---|---|
| GC08 | 17 | 79 | 47 |
| GC09 | 2 | quant. | 66 |
| GC11 | 42 | 6 | 7 |
| GB15 | 45.5 | 99 | 52 |

Example 13

Asymmetric Synthesis by using GD02, GD06, GD10 or GD12

The asymmetric synthesis procedure of Example 12 was repeated except that GA08 was changed to GA02. Also, GD06, GD10 or GD12 was used for conducting similar asymmetric synthesis. These results are shown in Table 12.

TABLE 12

| Chiral Broensted acid | Reaction time hr | Yield % | % ee |
|---|---|---|---|
| GD02 | 22.5 | quant. | 16 |
| GD06 | 46 | 83 | 48 |
| GD10 | 44 | quant. | 81 |
| GD12 | 46.5 | 84 | 68 |

Example 14

Asymmetric Synthesis by using GC02: Investigation of Imine Compounds

A Mannich adduct was asymmetrically synthesized from one of imine compounds (formula (32) below) shown in Table 13 and MK01 using GC02 as a catalyst. The result is shown in Table 13. Here, conditions for the asymmetric synthesis were the same as those shown in Example 12.

TABLE 13

| Entry | Imine compound R = | Reaction time hr | Yield % | % ee | Synthesized compound |
|---|---|---|---|---|---|
| 1 | Ph | 13 | 98 | 89 | 4aa |
| 2 | 4-FC$_6$H$_4$ | 10 | quant. | 85 | 4ga |
| 3 | 4-ClC$_6$H$_4$ | 24 | quant. | 80 | 4ha |
| 4 | 4-BrC$_6$H$_4$ | 35 | quant. | 76 | 4ia |
| 5 | 4-NO$_2$C$_6$H$_4$ | 46 | 40 | 78 | 4ja |
| 6 | 1-naphthyl | 31 | 92 | 39 | 4ka |
| 7 | 2-MeC$_6$H$_4$ | 42 | 84 | 51 | 4la |
| 8 | 4-MeC$_6$H$_4$ | 35 | quant. | 89 | 4ma |
| 9 | 4-MeOC$_6$H$_4$ | 46.5 | 86 | 75 | 4na |
| 10 | 2-Furyl | 5 | 88 | 75 | 4oa |
| 11 | 2-Thienyl | 48 | 72 | 69 | 4pa |
| 12 | PHCH=CH | 34 | 98 | 80 | 4qa |

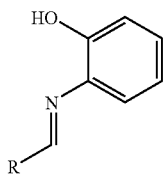

(32)

Compound of Entry 1 (4aa)
[α]$_D^{25}$ 0.2 (c1.03,CHCl$_3$).
Rf=0.4 (Hexane:Ethyl acetate=3:1)
$^1$H NMR (400 MHz,CDCl$_3$) δ=7.29-7.19 (m,5H), 6.69-6.49 (m,3H), 6.39-6.37 (m,1H), 5.80 (brs,1H), 4.93 (brs,1H), 4.57 (s,1H), 3.68 (s,3H), 1.24 (s,3H), 1.21 (s,3H).
$^{13}$C NMR (100 MHz,CDCl$_3$) δ=177.7, 144.3, 139.0, 135.5, 128.3, 127.9, 127.4, 121.0, 117.9, 114.3, 113.9, 64.6, 52.2, 47.4, 24.4, 20.0.
HPLC: Daicel Chiralpak AD-H, Hexane/i-PrOH=5/1, Flow rate=0.5 ml/min, UV=244 nm,
tR=11.1 min(3R), tR=16.0 min(3S).
Hereinafter, respective structures of compounds of Entries 2-12 were determined in the same way.

Compound of Entry 2 (4ga)
[α]$_D^{24}$-15.4 (c1.06,CHCl$_3$).
$^{19}$F NMR (400 MHz,CDCl$_3$)δ=-46.52.
MS m/z 317 (M$^+$), 217, 216, 215, 214, 120, 109.
Anal. Calcd for: C,68.12; H,6.35; N,4.41. Found: C,68.04; H,6.50; N,4.40.
HPLC: Daicel Chiralpak AD-H, Hexane/i-PrOH=5/1, Flow rate=0.5 ml/min, UV=244 nm,
tR=10.5 min (3R), tR=14.9 min (3S).

Compound of Entry 3 (4ha)
[α]$_D^{25}$-7.8 (c0.99,CHCl$_3$).
Rf=0.3 (Hexane:Ethyl acetate=3:1)
HPLC: Daicel Chiralpak AD-H, Hexane/i-PrOH=5/1, Flow rate=0.5 ml/min, UV=244 nm,
tR=10.2 min (3R), tR=15.7 min (3S).

Compound of Entry 4 (4ia)
[α]$_D^{20}$ 9.0 (c1.15,CHCl$_3$). oil.
Rf=0.4 (Hexane:Ethyl acetate=3:1)
Anal. Calcd for: C,57.15; H,5.33; N,3.70. Found: C,57.37; H,5.08; N,3.32.
HPLC: Daicel Chiralcel OD-H, Hexane/i-PrOH=15/1, Flow rate=0.5 ml/min, UV=244 nm,
tR=18.9 min (3S), tR=22.0 min (3R).

Compound of Entry 5 (4ja)
[α]$_D^{24}$ 22.9 (c0.53,CHCl$_3$). amorphous.
Rf=0.2 (Hexane:Ethyl acetate=3:1)
Anal. Calcd for: C,62.78; H,5.85; N,8.13. Found: C,62.75; H,5.97; N,7.97.
HPLC: Daicel Chiralpak OD-H, Hexane/i-PrOH=15/1, Flow rate=0.5 ml/min, UV=244 nm,
tR=38.2 min (3S), tR=42.3 min (3R).

Compound of Entry 6 (4ka)
[α]$_D^{25}$-90.5 (c1.07,CHCl$_3$).
Rf=0.3 (Hexane:Ethyl acetate=3:1)
HPLC: Daicel Chiralpak OD-H, Hexane/i-PrOH=15/1, Flow rate=0.5 ml/min, UV=244 nm,
tR=18.6 min (3S), tR=22.0 min (3R).

Compound of Entry 7 (4la)
Rf=0.3 (Hexane:Ethyl acetate=3:1)
HPLC: Daicel Chiralpak AD-H, Hexane/i-PrOH=5/1, Flow rate=0.5 ml/min, UV=244 nm,
tR=11.5 min (3R), tR=18.8 min (3S).

Compound of Entry 8 (4ma)
[α]$_D^{24}$ 16.2 (c0.99,CHCl$_3$). oil.
Anal. Calcd for: C,72.82; H,7.40; N,4.47. Found: C,72.98; H,7.54; N,4.53.
HPLC: Daicel Chiralpak AD-H, Hexane/i-PrOH=5/1, Flow rate 0.6 ml/min, UV=244 nm,
tR=8.3 min (3R), tR=13.6 min (3S).

Compound of Entry 9 (4na)
[α]$_D^{24}$ 8.9 (c0.99,CHCl$_3$). oil.
Rf=0.3 (Hexane:Ethyl acetate=3:1)
Anal. Calcd for: C,69.28; H,7.04; N,4.25. Found: C,69.42; H,6.92; N,4.23.
HPLC: Daicel Chiralpak AD-H, Hexane/i-PrOH=5/1, Flow rate=0.7 ml/min, UV=244 nm,
tR=8.9 min (3R), tR=16.8 min (3S).

Compound of Entry 10 (4oa)
[α]$_D^{24}$-52.2 (c0.92,CHCl$_3$). amorphous.
Rf=0.4 (Hexane:Ethyl acetate=5:1)
Anal. Calcd for: C,66.42; H,6.62; N,4.84. Found: C,66.66; H,6.52; N,4.91.
HPLC: Daicel Chiralpak AD-H, Hexane/i-PrOH=15/1, Flow rate=0.5 ml/min, UV=244 nm,
tR=22.9 min (3R), tR=26.7 min (3S).

Compound of Entry 11 (4pa)
[α]$_D^{24}$-12.5 (c1.06,CHCl$_3$). amorphous.
Rf=0.4 (Hexane:Ethyl acetate=3:1)
Anal. Calcd for: C,62.93; H,6.27; N,4.59; S,10.50. Found: C,62.96; H,6.39; N,4.51; S,10.66.
HPLC: Daicel Chiralpak AD-H, Hexane/i-PrOH=10/1, Flow rate=0.5 ml/min, UV=244 nm,
tR=20.1 min (3R), tR=23.9 min (3S).

Compound of Entry 12 (4qa)
[α]$_D^{20}$ 102.1 (c0.95,CHCl$_3$). amorphous.
Anal. Calcd for: C,73.82; H,7.12; N,4.30. Found: C,73.95; H,7.27; N,4.09.
HPLC: Daicel Chiralpak AS-H, Hexane/i-PrOH=15/1, Flow rate=0.5 ml/min, UV=244 nm,
tR=20.7 min (3S), tR=24.6 min (3R).

Example 15

Investigation of Nucleophilic Agents in Asymmetric Mannich Reactions

One of nucleophilic agents (formula (33) below) shown in Table 14 and MI01 were used to conduct asymmetric synthesis of a Mannich adduct, using GC02 as a catalyst. The result is shown in Table 14. Here, conditions for the asymmetric synthesis were the same as those shown in Example 12.

TABLE 14

| | $R_1$ | $R_2$ | $R_3$ | $R_4$ | Reaction temperature | Reaction time | Yield % | % ee | Synthesized compound |
|---|---|---|---|---|---|---|---|---|---|
| 1 | Me | Me | TMS | OMe | −78° C. | 13 | 98 | 89 | 4aa |
| 2 | Me | Me | TMS | OEt | −78° C. | 23 | quant. | 79 | 4ab |
| 3 | Me | Me | TMS | OiPr | −78° C. | 30 | 26 | 39 | 4ac |
| 4 | Me | Me | TBS | OMe | −78° C. | 23 | 45 | 76 | 4aa |
| 5 | H | H | TBS | OMe | −40° C. | 22.5 | 29 | 62 | 4ae |
| 6 | H | H | TMS | SEt | −78° C. | 46 | 97 | 45 | 4ag |

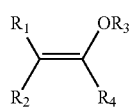
(33)

Compound of Entry 5 (4ae)
Rf=0.2 (Hexane:Ethyl acetate=3:1)
HPLC: Daicel Chiralpak AS-H, Hexane/i-PrOH=10/1, Flow rate=0.5 ml/min, UV=244 nm,
tR=39.6 min (3R), tR=44.1 min (3S).

Compound of Entry 6 (4ag)
Rf=0.3 (Hexane:Ethyl acetate=5:1)
HPLC: Daicel Chiralpak AS-H, Hexane/i-PrOH=9/1, Flow rate=0.5 ml/min, UV=244 nm,
tR=23.4 min (3R), tR=29.7 min (3S).

Example 16

Investigation of Diastereo-Selective Mannich Reactions: Investigation of Nucleophilic Agents One of nucleophilic agents (formula (34) below) shown in Table 15 and MI01 were used to conduct synthesis of respective diastereo-selective Mannich adducts (formulae (35) and (36) below) using GC02 as a catalyst. The result is shown in Table 15. Here, conditions for the asymmetric synthesis were the same as those shown in Example 12. As for the nucleophilic agent, one having E/Z=87/13 was used in Entry 1, one having E/Z=91/9 was used in Entries 2 and 3, and one having E/Z=96/4 was used in Entry 4.

TABLE 15

| Entry | $R_5$ | $R_6$ | Reation time | Yield % | syn/anti | % ee (syn/anti) | Synthesized compound |
|---|---|---|---|---|---|---|---|
| 1 | Me | Et | 17 | quant. | 87/13 | 96/— | 4ai |
| 2 | Bn | Et | 19 | quant. | 93/7 | 91/— | 4aj |
| 3 | TPSO | Me | 6 | 79 | 100/0 | 91/— | 4ak |
| 4 | TBSO | Me | 1 | 96 | 94/6 | 85/59 | 4al |

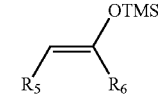
(34)

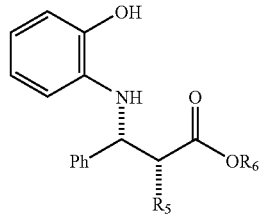
(35)

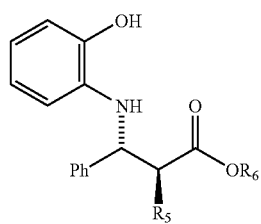
(36)

Compound of Entry 1 (4ai, syn/anti=87/13)
Rf=0.2 (Hexane:Ethyl acetate=3:1)
Anal. Calcd for: C,72.22; H,7.02; N,4.68. Found: C,72.37; H,7.29; N,4.56.
HPLC: Daicel Chiralpak AS-H, Hexane/i-PrOH=30/1, Flow rate=0.55 ml/min, UV=244 nm,
tR=48.3 min (2S,3R), tR=56.7 min (2R,3S).

Compound of Entry 2 (4aj, syn/anti=93/7)
Rf=0.3 (Hexane:Ethyl acetate=3:1)
Anal. Calcd for: C,76.77; H,6.71; N,3.73. Found: C,76.54; H,6.64; N,3.79.
HPLC: Daicel Chiralpak AS-H, Hexane/i-PrOH=30/1, Flow rate=0.5 ml/min, UV=244 nm,
tR=54.9 min (2S,3R), tR=64.4 min (2R,3S).

Compound of Entry 3 (4ak, syn/anti=100/0)
$[\alpha]_D^{25}$ 27.8 (c1.03,CHCl$_3$) (91% ee).
amorphous.
Anal. Calcd for: C,74.83; H,5.73; N,2.57. Found: C,74.54; H,5.61; N,2.37.
HPLC: Daicel Chiralpak AS-H, Hexane/EtOH=50/1, Flow rate=0.5 ml/min, UV=244 nm,
tR=37.8 min (2S,3R), tR=42.9 min (2R,3S).

Compound of Entry 4 (4al, syn/anti=94/6)
Rf=0.4 (Hexane:Ethyl acetate=3:1)
Anal. Calcd for: C,65.80; H,7.78; N,3.49. Found: C,65.96; H,7.49; N,3.34.
HPLC: Daicel Chiralpak AD-H, Hexane/EtOH=25/1, Flow rate=0.5 ml/min, UV=244 nm,
tR=11.1 min (2S,3R), tR=17.4 min (2R,3S).

Example 17

Investigation of Diastereo-Selective Mannich Reactions: Investigation of Imine Compounds One of imine compounds (formula (32) above) shown in Table 16 and one of nucleophilic agents (formula (37) below) were used to conduct synthesis of respective diastereo-selective Mannich adducts (formula (38) and formula (39) below)

using GC02 as a catalyst. The result is shown in Table 16. Here, conditions for the asymmetric synthesis were the same as those shown in Example 12. As for the nucleophilic agent, one having E/Z=87/13 was used in Entries 1-7, one having E/Z=87/13 was used in Entries 8-11, one having E/Z=91/9 was used in Entry 12, and one having E/Z=96/4 was used in Entries 13-14.

TABLE 16

| Entry | R | $R_5$ | $R_6$ | Reaction time | Yield % | syn/anti | % ee (syn/anti) | Synthesized compound |
|---|---|---|---|---|---|---|---|---|
| 1 | Ph | Me | Et | 17 | quant. | 87/13 | 96/— | 4ai |
| 2 | 4-FC$_6$H$_4$ | Me | Et | 3.5 | quant. | 91/9 | 84/36 | 4gi |
| 3 | 4-ClC$_6$H$_4$ | Me | Et | 7 | quant. | 86/14 | 83/14 | 4hi |
| 4 | 4-MeC$_6$H$_4$ | Me | Et | 22 | quant. | 94/6 | 81/35 | 4mi |
| 5 | 4-MeOC$_6$H$_4$ | Me | Et | 24 | quant. | 92/8 | 88/38 | 4ni |
| 6 | 2-Thienyl | Me | Et | 41 | 85 | 94/6 | 88/3 | 4pi |
| 7 | PhCH═CH | Me | Et | 37 | 91 | 95/5 | 90/49 | 4qi |
| 8 | Ph | Bn | Et | 19 | quant. | 93/7 | 91/— | 4aj |
| 9 | 4-MeOC$_6$H$_4$ | Bn | Et | 43.5 | 92 | 93/7 | 87/23 | 4nj |
| 10 | 4-FC$_6$H$_4$ | Bn | Et | 10 | 98 | 87/13 | 81/20 | 4gi |
| 11 | PhCH═CH | Bn | Et | 46.5 | 65 | 95/5 | 90/15 | 4qi |
| 12 | Ph | TPSO | Me | 6 | 79 | 100/0 | 91/— | 4ak |
| 13 | 4-MeOC$_6$H$_4$ | TPSO | Me | 46 | 98 | 100/0 | 84/— | 4nk |
| 14 | PhCH═CH | TPSO | Me | 46 | 86 | 100/0 | 91/— | 4qk |

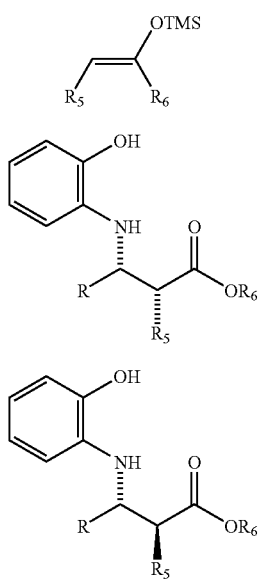

(37)

(38)

(39)

Compound of Entry 2 (4gi, syn/anti=91/9)

Rf=0.3 (Hexane:Ethyl acetate=3:1)
$^{19}$F NMR (376 MHz,CDCl$_3$) δ=46.74 (s,anti),46.29 (s,syn).
Anal. Calcd for: C,68.12; H,6.35; N,4.41. Found: C,67.90; H,6.35; N,4.31.
HPLC: Daicel Chiralcel OJ-H, Hexane/i-PrOH=9/1, Flow rate=0.7 ml/min, UV=244 nm,
tR=43.2 min (2S,3R), tR=56.2 min (2R,3S).

Compound of Entry 3 (4hi, syn/anti=86/14)
Rf=0.3 (Hexane:Ethyl acetate=3:1)
Anal. Calcd for: C,64.77; H,6.04; N,4.20. Found: C,64.56; H,5.81; N,4.19.
HPLC: Daicel Chiralpak AD-H, Hexane/i-PrOH=30/1, Flow rate=0.5 ml/min, UV=244 nm,
tR=62.4 min (2S,3R), tR=73.8 min (2R,3S).

Compound of Entry 4 (4mi, syn/anti=94/6)
Rf=0.3 (Hexane:Ethyl acetate=3:1)
Anal. Calcd for: C,72.82; H,7.40; N,4.47. Found: C,72.75; H,7.75; N,4.35.
HPLC: Daicel Chiralpak AD-H, Hexane/EtOH=40/1, Flow rate=0.5 ml/min, UV=244 nm,
tR=46.4 min (2S,3R), tR=56.2 min (2R,3S).

Compound of Entry 5 (4ni, syn/anti=92/8)
Rf=0.2 (Hexane:Ethyl acetate=3:1)
Anal. Calcd for: C,69.28; H,7.04; N,4.25. Found: C,69.11; H,6.73; N,4.09.
HPLC: Daicel Chiralcel OJ-H, Hexane/EtOH=5/1, Flow rate=0.8 ml/min, UV=244 nm,
tR=22.4 min (2S,3R), tR=29.8 min (2R,3S).

Compound of Entry 6 (4pi, syn/anti=94/6)
Rf=0.3 (Hexane:Ethyl acetate=3:1)
Anal. Calcd for: C,62.93; H,6.27; N,4.59; S,10.50. Found: C,62.55; H,6.49; N,4.25; S,10.39.
HPLC: Daicel Chiralcel OD-H, Hexane/i-PrOH=40/1, Flow rate=0.5 ml/min, UV=244 nm,
tR=69.7 min (2S,3R), tR=80.7 min (2R,3S).

Compound of Entry 7 (4qi, syn/anti=95/5)
Rf=0.3 (Hexane:Ethyl acetate=3:1)
Anal. Calcd for: C,73.82; H,7.12; N,4.30. Found: C,73.43; H,6.97; N,4.15.
HPLC: Daicel Chiralcel OD-H, Hexane/i-PrOH=15/1, Flow rate=0.5 ml/min, UV=244 nm,
tR=29.3 min (2S,3R), tR=33.5 min (2R,3S).

Compound of Entry 9 (4nj, syn/anti=93/7)
Rf=0.3 (Hexane:Ethyl acetate=3:1)
Anal. Calcd for: C,74.05; H,6.71; N,3.45. Found: C,74.22; H,6.87; N,3.25.
HPLC: Daicel Chiralpak AD-H, Hexane/i-PrOH=5/1, Flow rate=0.5 ml/min, UV=244 nm,
tR=21.7 min (2S,3R), tR=34.7 min (2R,3S).

Compound of Entry 10 (4gj, syn/anti=87/13)
Rf=0.2 (Hexane:Ethyl acetate=5:1)
Anal. Calcd for: C,73.26; H,6.15; N,3.56. Found: C,73.31; H,6.52; N,3.30.

HPLC: Daicel Chiralpak AD-H, Hexane/EtOH=10/1, Flow rate=0.5 ml/min, UV=244 nm,
tR=23.4 min (2S,3R), tR=27.0 min (2R,3S).

Compound of Entry 11 (4qj, syn/anti=95/5)
Rf=0.4 (Hexane:Ethyl acetate=3:1)
Anal. Calcd for: C,77.78; H,6.78; N,3.49. Found: C,77.66; H,6.56; N,3.19.
HPLC: Daicel Chiralcel OD-H, Hexane/i-PrOH=30/1, Flow rate=1.0 mil/min, UV=244 nm,
tR=30.6 min (2S,3R), tR=58.2 min (2R,3S).

Compound of Entry 13 (4nk, syn/anti=100/0)
$[\alpha]_D^{25}$ 12.1 (c0.91,CHCl$_3$,84% ee). oil.
Rf=0.2 (Hexane:Ethyl acetate=5:1)
Anal. Calcd for: C,73.02; H,5.78; N,2.43. Found: C,73.29; H,5.76; N,2.33.
HPLC: Daicel Chiralcel OD-H, Hexane/i-PrOH=20/1, Flow rate=0.5 ml/min, UV=244 nm,
tR=20.8 min (2R,3S), tR=23.7 min (2S,3R).

Example 18

Asymmetric Hydrophosphorylation Reaction 0.118 mM of one of imine compounds represented by formula (40) below (a group for Ar is shown in Table 17, for example, N-2-nitrobenzylidene4-methoxyaniline was used in Entry 1), GC11 (0.035 mM) as a chiral Broensted acid catalyst, and toluene (1 mL) were put in a dried two-necked round bottom flask (10 mL) under nitrogen atmosphere and stirred at room temperature for 10 minutes. After that, diisopropylphosphite (0.173 mM) was added dropwise, and the reaction mixture was stirred for 24 hours. The reaction was quenched by the addition of a saturated aqueous sodium hydrogen carbonate solution. The reaction mixture was extracted with ethyl acetate three times. The extract was washed with a saturated salt solution, and dried over anhydrous sodium sulfate. After the drying, the extract was filtered. The filtrate was concentrated under a reduced pressure, which was separated and purified by means of p-TLC (n-hexane:ethyl acetate) to give the compound represented by formula (41) (Entry 1: n-hexane:ethyl acetate=1:1, Rf=0.3; 35.6 mg, 0.085 mM, yield: 72%, 77% ee). Optical purity thereof was determined by means of high-performance mixture chromatography. These results are shown in Table 17.

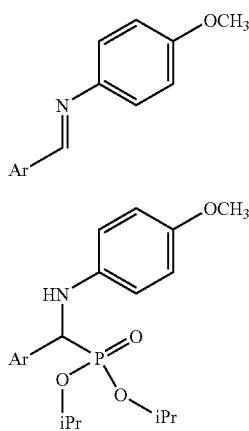

TABLE 17

| Entry | Imine compound Ar = | Reaction time hr | Yield % | % ee | Synthesized compound |
|---|---|---|---|---|---|
| 1 | 2-NO$_2$C$_6$H$_4$ | 24 | 72 | 77 | PP01 |
| 2 | 4-FC$_6$H$_4$ | 24 | 80 | 50 | PP02 |
| 3 | Ph | 24 | 90 | 56 | PP03 |
| 4 | 1-Furyl—CH=CH | 24 | 44 | 70 | PP04 |
| 5 | 1-Furyl | 24 | 79 | 61 | PP05 |
| 6 | 2-MeC$_6$H$_4$ | 24 | 78 | 69 | PP06 |
| 7 | 2-MeOC$_6$H$_4$ | 24 | <97 | 60 | PP07 |
| 8 | C$_6$H$_5$—CH=CH | 24 | 49 | 80 | PP08 |
| 9 | 4-MeC$_6$H$_4$ | 24 | 69 | 51 | PP09 |

Compound of Entry 1 (PP01)
$^1$H NMR (400 MHz,CDCl$_3$) δ=7.98 (d,1H,J=7.50 Hz), 7.71 (d,1H,J=4.94 Hz), 7.54 (t,1H,J=7.0 Hz), 7.40 (d,1H, J=8.24 Hz), 6.73 (d,2H,J=8.78 Hz), 6.62 (d,2H,J=8.60 Hz), 6.05 (dd,1H,J=8.78,17.39 Hz), 4.70-4.75 (m,2H),4.52-4.57 (m,1H), 3.69 (s,3H), 1.31 (d,3H,J=6.22 Hz), 1.27 (d,3H, J=6.22 Hz), 1.22 (d,3H,J=6.04 Hz), 0.90 (d,3H,J=6.22 Hz).
HPLC: Daicel Chiralcel OD-H, Hexane/i-PrOH=60/1, Flow rate=0.3 ml/min, UV=254 nm,
tR=47.8 min (major), tR=52.2 min (minor).

Compound of Entry 2 (PP02)
$^1$H NMR (400 MHz,CDCl$_3$) δ=7.40-7.44 (m,2H), 7.00 (t,2H,J=8.60 Hz), 6.69 (d,J=8.78 Hz), 6.51 (d,J=8.78 Hz), 4.46 -4.71 (m,4H), 3.68 (s,3H), 1.31 (d,3H,J=6.22 Hz), 1.27 (d,3H,J=6.04 Hz), 1.22 (d,3H,J=6.22 Hz), 0.98 (d,3H,J=6.22 Hz).

Compound of Entry 3 (PP03)
$^1$H NMR (400 MHz,CDCl$_3$) δ=7.43-7.46 (m,2H), 7.30 (t,2H,J=7.64 Hz), 7.24 (t,1H,J=2.01,5.67 Hz), 6.78 (dt,2H, J=2.38,4.39 Hz), 6.53 (dt,2H,J=2.38,4.39 Hz),4.43-4.71 (m,4H), 3.68 (s,3H), 1.31 (d,2H,J=6.22 Hz), 1.25 (d,2H, J=6.04 Hz), 1.22 (d,2H,J=6.22 Hz), 0.92 (d,2H,J=6.22 Hz).

Compound of Entry 4 (PP04)
$^1$H NMR (400 MHz,CDCl$_3$) δ=7.31 (s,1H), 6.75 (d,2H, J=8.78 Hz), 6.62 (d,2H,J=8.78 Hz), 6.49 (dd,1H,J=5.03, 10.98 Hz), 6.34 (s,1H), 6.18-6.25 (m,2H), 4.70-4.76 (m,2H), 4.26 (dt,J=6.96,13.18 Hz), 4.01 (t,J=8.42 Hz), 3.74 (s,3H), 1.33-1.35 (m,6H), 1.28 (d,3H,J=6.04 Hz), 1.25 (d,3H,J=6.22 Hz).

Compound of Entry 5 (PP05)
$^1$H NMR (400 MHz,CDCl$_3$) δ=7.36 (d,1H,J=0.73 Hz), 6.73 (d,2H,J=2.20 Hz), 6.72 (d,2H,J=2.38 Hz), 6.34 (t,2H, J=3.11,3.29 Hz), 4.68-6.80 (m,2H), 4.55-4.60 (dd,1H, J=6.22,7.14 Hz), 4.26 (t,1H,J=7.14 Hz), 3.71 (s,3H), 1.34 (d,3H,J=6.22 Hz), 1.30 (d,3H,J=6.22 Hz), 1.27 (d,3H,J=6.22 Hz), 1.07 (d,3H,J=6.04 Hz).

Compound of Entry 6 (PP06)
$^1$H NMR (400 MHz,CDCl$_3$) δ=7.47 (d,1H,J=2.38 Hz), 7.09-7.15 (m,3H), 6.65-6.81 (m,2H), 6.45-6.49 (m,2H), 4.84 (dd,1H,J=7.32,16.84 Hz), 4.68-4.75 (m,1H), 4.59 (t,1H, J=8.24,7.87 Hz), 4.34-4.41 (m,1H), 3.67 (s,3H), 2.49 (s,3H), 1.32 (d,3H,J=6.04 Hz), 1.26 (dd,6H,J=6.22,3.66 Hz), 0.79 (d,3H,J=6.22 Hz).

Compound of Entry 7 (PP07)
$^1$H NMR (400 MHz,CDCl$_3$) δ=7.44 (dt,1H,J=2.47,1.50, 3.66 Hz), 7.20 (t,1H,J=8.24,5.49 Hz), 6.90 (t,1H,J=7.60 Hz), 6.87 (d,1H,J=8.42 Hz), 6.66 (d,2H,J=6.59 Hz), 6.56 (d,2H, J=6.77 Hz), 5.25 (dd,1H,J=9.52,9.15 Hz), 4.75-4.80 (m,1H), 4.75 (t,1H,J=8.97 Hz), 4.35-4.40 (m,1H), 3.90 (s,3H), 3.67

(s,3H), 1.32 (d,3H,J=6.22 Hz), 1.27 (d,3H,J=6.22 Hz), 1.20 (d,3H,J=6.22 Hz), 0.80 (d,3H,J=6.22 Hz).

Compound of Entry 8 (PP08)

¹H NMR (400 MHz,CDCl₃) δ=7.33 (d,2H,J=7.69 Hz), 7.28 (d,2H,J=7.69 Hz), 7.20 (dd,1H,J=7.32,6.77 Hz), 6.73 (d,2H,J=8.97 Hz), 6.63 (d,2H,J=8.78 Hz), 6.25 (dd,1H, J=4.94,6.04,5.12 Hz), 4.71-4.79 (m,1H), 4.29 (ddd,1H,J=6.8, 8.8,12.4 Hz), 4.01 (dd,1H,J=8.60,8.05 Hz), 3.73 (s,3H), 1.34 (d,6H,J=6.22 Hz), 1.22-1.27 (m,6H).

Compound of Entry 9 (PP09)

¹H NMR (400 MHz,CDCl₃) δ=7.32 (dd,2H,J=2.19,6.04 Hz), 7.10 (d,2H,J=8.05 Hz), 6.67 (dd,2H,J=2.19,4.39 Hz), 6.53 (dd,2H,J=2.19,4.57 Hz), 6.89 (m,1H), 4.44-4.61 (m,3H), 3.07 (s,3H), 2.30 (s,3H), 1.31 (d,3H,J=6.22 Hz), 1.26 (d,3H,J=6.04 Hz), 1.23 (d,3H,J=6.22 Hz), 0.95 (d,3H,J=6.22 Hz).

Example 19

Asymmetric aza Diels-Alder Reaction: Investigation of Solvent

MI01 (0.15 mM), GC11 (0.1 eq.) and one of solvents shown in Table 18 (1.0 mL) were put in a dried two-necked round bottom flask (10 mL) under nitrogen atmosphere and stirred at −78° C. for 10 minutes. 1-Methoxy-3-trimetylsiloxy-1,3-butadiene (Danishefsky'diene, 0.3 mM) was added dropwise over 2 minutes. After checking decrease in color of MI01 (detected with 2,4-dinitrophenylhydrazine) by means of TLC, a saturated aqueous sodium hydrogen carbonate solution and a saturated aqueous potassium fluoride solution was added dropwise thereto in this order. Then, the mixture was stirred for additional 30 minutes at room temperature. After that, the reaction mixture was filtered over celite. Then, the filtrate was extracted with dichloromethane three times. The organic layer was washed with 1 N hydrochloric acid and a saturated salt solution followed by drying over anhydrous sodium sulfate. After the drying, the crude liquid obtained by concentrating the filtrate was purified by means of p-TLC to give 1-(2-hydroxyphenyl)-2-phenyl-1,2,3,4-tetrahydropyridin-4-one (PDA01).

The result obtained for each solvent is shown in Table 18.

Rf=0.3(silica gel, chloroform/isopropanol=19/1)

¹H NMR (400 MHz,CDCl₃) δ=9.50 (brs,1H), 7.43 (d,1H, J=7.6 Hz), 7.26-6.66 (m,9H), 5.30 (dd,1H,J=6.7,7.1 Hz), 5.24 (d,1H,J=7.6 Hz), 3.25 (dd,1H,J=7.1,17.0 Hz), 2.87 (dd, 1H,J=6.7,17.0 Hz).

HPLC: Daicel Chiralpack AD-H, n-hexane/ethanol=10/1, flow rate=0.5 ml/min tR=28.6 min (R), tR=33.8 min (S)

The absolute configuration of R-form and S-form was determined by comparing with literature values after inducing PDA01 to 1-(2-benzoloxyphenyl)-2-phenyl-1,2,3,4-tetrahydropyridin-one.

1-(3-methoxyphenyl)-2-phenyl-1,2,3,4-tetrahydropyridin-one

Rf=0.3 (silica gel, n-hexane/ethyl acetate=1/2)

¹H NMR (400 MHz,CDCl₃) δ=7.68 (dd,1H,J=7.9 Hz,1.1 Hz), 7.34-7.18 (m,6H), 6.66-6.54(m,3H), 5.29-5.26 (m,2H), 3.73 (s,3H), 3.30 (dd,1H,J=16.4 Hz,7.1 Hz), 2.78 (ddd,1H, J=16.4 Hz,2.9 Hz,1.1 Hz).

HPLC: Daicel Chiralpack AD-H, n-hexane/ethanol=10/1, flow rate=0.5 ml/min tR=36.5 min (R), tR=42.3 min

TABLE 18

| Entry | Solvent | Temperature ° C. | Yield % | % ee |
|---|---|---|---|---|
| 1 | Toluene | −78 | 32 | 42(S) |
| 2 | Ethylbenzene | −78 | 62 | 42(S) |
| 3 | Mesitylene | −40 | <99 | 49(S) |
| 4 | Diethylether | −78 | 33 | 18(R) |
| 5 | Dichloromethane | −78 | 63 | 41(R) |
| 6 | Nitromethane | −25 | <99 | 26(R) |
| 7 | Methanol | −78 | 91 | 11(R) |
| 8 | DMF | −58 | <72 | 8(R) |

Example 20

Asymmetric aza Diels-Alder Reaction: Investigation of Imine Compound

The procedure of Example 19 was repeated to give a chiral compound represented by formula (43) except that the conditions was changed to an imine compound in which one of Ar in Table 19 is bonded in formula (42) below (for example, in the case of Entry 1, a 2-hydroxyphenyl group is bonded in formula (42)), Mesitylene as a solvent, −40° C. as a reaction temperature, and 19.5 hours as a reaction time. These results are shown in Table 19. Here, Entry 1 in Example 20 is the same as that in Example 19.

TABLE 19

| Entry | Imine compound Ar = | Yield % | % ee | Synthesized compound |
|---|---|---|---|---|
| 1 | 2-OHC₆H₄ | <99 | 49 | PDA01 |
| 2 | 3-OMe—C₆H₄ | 33 | 15 | PDA02 |
| 3 | 4-OMe—C₆H₄ | 18 | 20 | PDA03 |
| 4 | 2-OH, 5-MeC₆H₃ | 61 | 52 | PDA04 |

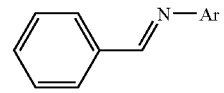

(42)

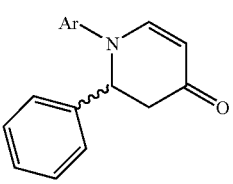

(43)

Compound of Entry 2 (PDA02;1-(3-methoxyphenyl)-2-phenyl-1,2,3,4-tetrahydropyridin-4-one)

Rf=0.3 (silica gel, n-hexane/ethyl acetate=1/2)

¹H NMR (400 MHz,CDCl₃) δ 7.68 (dd,1H,J=7.9 Hz,1.1 Hz), 7.34-7.18 (m,6H), 6.66-6.54 (m,3H), 5.29-5.26 (m,2H), 3.73 (s,3H), 3.30 (dd,1H,J=16.4 Hz,7.1 Hz), 2.78 (ddd,1H, J=16.4 Hz,2.9 Hz,1.1 Hz).

HPLC: Daicel Chiralpack AD-H, n-hexane/ethanol=10/1, flow rate=0.5 ml/min tR=36.5 min (R), tR=42.3 min Compound of Entry 3 (PDA03;1-(4-methoxyphenyl)-2-phenyl-1,2,3,4-tetrahydropyridin-4-one)

Rf=0.2 (silica gel, n-hexane/ethyl acetate=1/1).
$^{1}$H NMR (400 MHz,CDCl$_{3}$) δ 7.55 (d,1H,J=7.6 Hz), 7.33-7.25 (m,5H), 6.96-6.94 (m,2H), 6.81-6.79 (m,2H), 5.23 (d,1H,J=7.6 Hz), 5.18 (dd,1H,J=8.0 Hz,4.0 Hz), 3.76 (s,3H), 3.26 (dd,1H,J=16.0 Hz,8.0 Hz, 2.76 (dd,1H,J=16.0 Hz,8.0 Hz).
HPLC: Daicel Chiralpack AD-H, n-hexane/ethanol=5/1, flow rate=0.5 ml/min
tR=36.3 min (R), tR=41.4 min.

Compound of Entry 4 (PDA04;1-(2-hydroxy-5-methyl-phenyl)-2-phenyl-1,2,3,4-tetrahydropyridin-4-one)

Rf=0.3 (silica gel, n-hexane/ethyl acetate=1/2)
$^{1}$H NMR (400 MHz,CDCl$_{3}$) δ 8.64 (1H,brs), 7.39 (1H,d, J=8.0 Hz), 7.26-7.19(m,5H), 6.80-6.70 (m,3H), 5.27 (dd,1H, 8.0 Hz,4.0 Hz), 5.21 (d,1H,J=8.0 Hz), 3.23 (dd,1H,J=16.0 Hz,8.0 Hz), 2.84 (dd,1H,J=16.0 Hz,4.0 Hz), 2.33 (s,3H).
HPLC: Daicel Chiralpack AD-H, n-hexane/ethanol=10/1, flow rate=0.5 ml/min
tR=29.1 min (R), tR=62.2 min.

INDUSTRIAL APPLICABILITY

The method of asymmetric synthesis employing the catalyst for asymmetric synthesis according to the invention can be used as a synthesis method that leads to a high optical purity. Further, by applying the method of asymmetric synthesis according to the invention to asymmetric Mannich reactions and the like, it is possible to obtain compounds that are used as medical drugs, agricultural chemicals and the like, and compounds that are useful as an intermediate for synthesizing them.

The invention claimed is:
1. A method of asymmetric synthesis comprising:
a step of preparing a chiral binaphthol-phosphoric acid compound or a chiral 5,5',6,6',7,7',8,8'-octahydrobinaphthol-phosphoric acid compound as a Broensted acid catalyst, and
a step of synthesizing a chiral compound by an asymmetric reaction using the Broensted acid catalyst,
wherein the asymmetric reaction is a reaction selected from the group consisting of an asymmetric Mannich reaction, an asymmetric hydrophosphorylation reaction, an asymmetric aza Diels-Alder reaction,
wherein the chiral binapthol-phosphoric acid compound is a compound represented by formula (1) below or the chiral 5,5',6,6',7,7',8,8'-octahydrobinaphthol-phosphoric acid compound is a compound represented by formula (3) below:

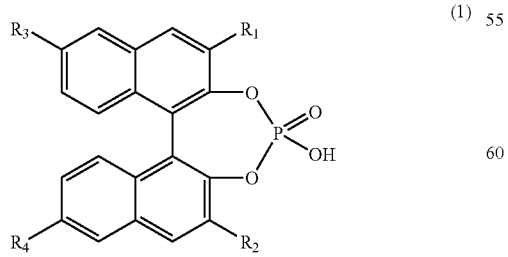

(1)

wherein R$_{1}$, R$_{2}$, R$_{3}$, and R$_{4}$ may be independent of each other, and denote a hydrogen atom; a halogen atom; a nitro group; a monohalogenomethyl group; a dihalogenomethyl group; a trihalogenomethyl group; a nitrile group; a formyl group; —COA$_{1}$ (A$_{1}$ denotes an optionally branched alkyl group having 1 to 6 carbons); —COOA$_{2}$ (A$_{2}$ denotes an optionally branched alkyl group having 1 to 6 carbons); an optionally branched alkyl group having 1 to 20 carbons; an optionally branched alkenyl group having 3 to 20 carbons; an optionally branched alkoxy group having 1 to 20 carbons; an aryl group selected from the group consisting of a phenyl group, a 1-naphthyl group, and a 2-naphthyl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —COA$_{1}$ (A$_{1}$ denotes an optionally branched alkyl group having 1 to 6 carbons), —COOA$_{2}$ (A$_{2}$ denotes an optionally branched alkyl group having 1 to 6 carbons), an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —COA$_{1}$ (A$_{1}$ denotes an optionally branched alkyl group having 1 to 6 carbons), —COOA$_{2}$ (A$_{2}$ denotes an optionally branched alkyl group having 1 to 6 carbons), and an optionally branched alkyl group having 1 to 20 carbons; a cycloalkyl group having 3 to 8 carbons; or formula (2) below,

(2)

wherein A$_{3}$, A$_{4}$, and A$_{5}$ may be independent of each other, and denote an optionally branched alkyl group having 1 to 6 carbons, a phenyl group, or a phenyl group mono- to tetra- substituted with an optionally branched alkyl group having 1 to 6 carbons,

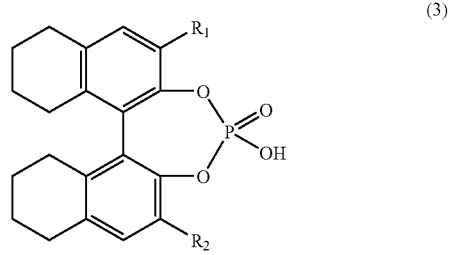

(3)

wherein R$_{1}$ and R$_{2}$ may be independent of each other, and denote a hydrogen atom; a halogen atom; a nitro group; a monohalogenomethyl group; a dihalogenomethyl group; a trihalogenomethyl group; a nitrile group; a formyl group; —COA$_{1}$ (A$_{1}$ denotes an optionally branched alkyl group having 1 to 6 carbons); —COOA$_{2}$ (A$_{2}$ denotes an optionally branched alkyl group having 1 to 6 carbons); an optionally branched alkyl group having 1 to 20 carbons; an optionally branched alkenyl group having 3 to 20 carbons; an optionally branched alkoxy group having 1 to 20 carbons; an aryl group; an aryl group mono- or di-substituted with an aryl group; an aryl group mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), —$COOA_2$ ($A_2$ denotes an optionally branched alkyl group having 1 to 6 carbons), an optionally branched alkyl group having 1 to 10 carbons, an optionally branched alkenyl group having 1 to 10 carbons, and an optionally branched alkoxy group having 1 to 20 carbons; an aryl group mono- or di-substituted with an aryl group that may be mono- to tetra-substituted with at least one type selected from the group consisting of a nitro group, a halogen atom, a monohalogenomethyl group, a dihalogenomethyl group, a trihalogenomethyl group, a nitrile group, a formyl group, —$COA_1$ ($A_1$ denotes an optionally branched alkyl group having 1 to 6 carbons), —$COOA_2$ ($A_2$ denotes an optionally branched alkyl group having 1 to 6 carbons), and an optionally branched alkyl group having 1 to 20 carbons; a cycloalkyl group having 3 to 8 carbons; or formula (2).

2. A method for producing a chiral amino compound from an imine compound and an enol compound by the method of asymmetric synthesis according to claim 1.

3. The method of asymmetric synthesis according to claim 1, wherein the asymmetric reaction is an asymmetric Mannich reaction using as a Broensted acid catalyst the compound of formula (1) or formula (3).

4. The method of asymmetric synthesis according to claim 1, wherein the asymmetric reaction is an asymmetric hydrophosphorylation reaction using as a Broensted acid catalyst the compound of formula (1) or formula (3).

5. The method of asymmetric synthesis according to claim 1, wherein the symmetric reaction is an asymmetric aza Diels-Alder reaction using as a Broensted acid catalyst the compound of formula (1) or formula (3).

* * * * *